(12) United States Patent
Pizzochero et al.

(10) Patent No.: US 11,241,529 B2
(45) Date of Patent: Feb. 8, 2022

(54) FLUID INTERCONNECTION SCHEME BETWEEN RESERVOIR, PUMP AND FILLING MEMBER

(71) Applicant: Becton, Dickinson and Company, Franklin Lakes, NJ (US)

(72) Inventors: Alessandro Pizzochero, Chelmsford, MA (US); J. Richard Gyory, Sudbury, MA (US); Joseph Iskandar, Allston, MA (US); Charles Hwang, Wellesley, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 439 days.

(21) Appl. No.: 15/761,380

(22) PCT Filed: Sep. 20, 2016

(86) PCT No.: PCT/US2016/052648
§ 371 (c)(1),
(2) Date: Mar. 19, 2018

(87) PCT Pub. No.: WO2017/053284
PCT Pub. Date: Mar. 30, 2017

(65) Prior Publication Data
US 2018/0272058 A1 Sep. 27, 2018

Related U.S. Application Data

(60) Provisional application No. 62/221,430, filed on Sep. 21, 2015.

(51) Int. Cl.
*A61M 5/14* (2006.01)
*A61M 5/142* (2006.01)
(Continued)

(52) U.S. Cl.
CPC ...... *A61M 5/1413* (2013.01); *A61M 5/14248* (2013.01); *A61M 5/162* (2013.01);
(Continued)

(58) Field of Classification Search
CPC .............. A61M 5/008; A61M 5/14248; A61M 5/14244; A61M 5/162; A61M 5/14566;
(Continued)

(56) References Cited

U.S. PATENT DOCUMENTS 4,013,074 A 3/1977 Siposs
4,557,722 A * 12/1985 Harris ............... A61M 5/14276
604/891.1
(Continued)

FOREIGN PATENT DOCUMENTS

CA 1137374 A 12/1982
DE 102007024801 A1 11/2008
(Continued)

*Primary Examiner* — James D Ponton
(74) *Attorney, Agent, or Firm* — Dickinson Wright PLLC

(57) ABSTRACT

A filling member (43) in a medicament delivery device (1), the filling member (43) includes a first conduit (12) that fluidly communicates with a reservoir (4) and a second conduit (14) that fluidly communicates with a pump (3) and with the first conduit (12), wherein the filling member (43) provides two-way medicament flow that enters the reservoir (4) via the first conduit (12), exits the reservoir (4) into the first conduit (12) and the second conduit (14), and exits the second conduit (14) to the pump (3). The reservoir (4) includes a reservoir tube (44A) having one end that is formed with the reservoir (4), and the reservoir tube (44A) having another end that is press fit to the filling member (43) to establish fluid communication with the reservoir (4).

14 Claims, 26 Drawing Sheets

(51) Int. Cl.
*A61M 5/145* (2006.01)
*A61M 5/168* (2006.01)
*A61M 5/162* (2006.01)

(52) U.S. Cl.
CPC ..... *A61M 5/14566* (2013.01); *A61M 5/14586* (2013.01); *A61M 5/1684* (2013.01); *A61M 2005/14252* (2013.01); *A61M 2005/14268* (2013.01); *A61M 2005/16863* (2013.01); *A61M 2205/3386* (2013.01); *A61M 2205/3561* (2013.01); *A61M 2205/3584* (2013.01); *A61M 2205/50* (2013.01); *A61M 2205/505* (2013.01); *A61M 2205/8206* (2013.01); *A61M 2209/045* (2013.01)

(58) Field of Classification Search
CPC .......... A61M 5/14586; A61M 5/16809; A61M 2005/14268; A61M 5/1413; A61M 2209/045; A61M 2039/0063; A61M 2039/0072; A61M 5/204
See application file for complete search history.

(56) References Cited

U.S. PATENT DOCUMENTS

| | | | |
|---|---|---|---|
| 4,626,244 A | 12/1986 | Reinicke | |
| 4,747,832 A | 5/1988 | Buffet | |
| 4,816,016 A | 3/1989 | Schulte et al. | |
| 5,176,641 A | 1/1993 | Idriss | |
| 5,707,361 A | 1/1998 | Slettenmark | |
| 5,957,895 A | 9/1999 | Sage et al. | |
| 6,589,229 B1 | 7/2003 | Connelly et al. | |
| 6,652,510 B2 | 11/2003 | Lord et al. | |
| 6,708,714 B1 | 3/2004 | Mijers | |
| 6,981,967 B2 | 1/2006 | Massengale et al. | |
| 7,637,897 B2 | 12/2009 | Ginggen | |
| 7,713,262 B2 | 5/2010 | Adams et al. | |
| 7,938,801 B2 | 5/2011 | Hawkins et al. | |
| 8,231,608 B2 | 7/2012 | Pang et al. | |
| 8,298,183 B2 | 10/2012 | Menot et al. | |
| 8,540,172 B2 | 9/2013 | Waterman et al. | |
| 8,603,051 B2 | 12/2013 | Kuo et al. | |
| 8,734,395 B2 | 5/2014 | McAllister | |
| D706,415 S | 6/2014 | Levesque et al. | |
| 8,821,443 B2 | 9/2014 | Levesque et al. | |
| 8,827,957 B2 | 9/2014 | Searle et al. | |
| 8,870,829 B2 | 10/2014 | Halili et al. | |
| 8,992,478 B2 | 3/2015 | Levesque | |
| 9,155,875 B2 | 10/2015 | McAllister | |
| 9,173,993 B2 | 11/2015 | Yodfat et al. | |
| 9,375,529 B2 | 6/2016 | Searle et al. | |
| 9,376,224 B2 | 6/2016 | Gonnelli et al. | |
| 9,381,299 B2 | 7/2016 | Kuo et al. | |
| 9,415,198 B2 | 8/2016 | McAllister | |
| 9,511,187 B2 | 12/2016 | Gonnelli et al. | |
| 9,636,451 B2 | 5/2017 | Gonnelli et al. | |
| 9,687,599 B2 | 6/2017 | Gonnelli et al. | |
| 9,795,735 B2 | 10/2017 | Levesque et al. | |
| 9,814,831 B2 | 11/2017 | Gonnelli | |
| 9,833,383 B2 | 12/2017 | Gonnelli et al. | |
| 9,968,731 B2 | 5/2018 | Gonnelli et al. | |
| 9,981,083 B2 | 5/2018 | Gonnelli et al. | |
| 2003/0208157 A1 | 11/2003 | Eidson et al. | |
| 2008/0058718 A1 | 3/2008 | Adams et al. | |
| 2009/0062768 A1 | 3/2009 | Saul | |
| 2009/0182286 A1* | 7/2009 | Wolfson | A61M 39/02 604/244 |
| 2010/0069891 A1 | 3/2010 | Ginggen | |
| 2011/0098676 A1 | 4/2011 | Chiang et al. | |
| 2014/0090746 A1 | 4/2014 | Kuehni et al. | |
| 2014/0135699 A1 | 5/2014 | Gyory | |
| 2014/0194812 A1 | 7/2014 | Amirouche | |
| 2014/0276538 A1* | 9/2014 | Michaud | A61M 5/14244 604/500 |
| 2015/0032051 A1 | 1/2015 | Brandt et al. | |
| 2015/0038906 A1* | 2/2015 | Cane' | A61M 5/14566 604/152 |
| 2016/0038672 A1 | 2/2016 | Brandt et al. | |
| 2016/0184515 A1 | 6/2016 | Shih et al. | |
| 2016/0206815 A1 | 7/2016 | Chong | |
| 2018/0036475 A1 | 2/2018 | Lin | |

FOREIGN PATENT DOCUMENTS

| | | |
|---|---|---|
| EP | 1549382 B1 | 3/2016 |
| JP | 3-39167 A | 2/1991 |
| WO | WO-2004/006981 A3 | 1/2004 |
| WO | WO-2015/091758 A1 | 6/2015 |

\* cited by examiner

FLUID INTERCONNECTION SCHEME BETWEEN RESERVOIR, PUMP AND FILLING MEMBER

This application claims the benefit under 35 U.S.C. § 119(e) of U.S. Provisional Patent Application Ser. No. 62/221,430, filed on Sep. 21, 2015, the entire content, disclosure and subject matter of this application being expressly incorporated herein by reference.

FIELD OF THE INVENTION

The present invention relates to medical devices, and more particularly, to medical devices with a filling member that is in fluid communication with a reservoir and a pump to deliver medicament to a patient.

BACKGROUND OF THE INVENTION

Diabetes is a group of diseases characterized by high levels of blood glucose resulting from the inability of diabetic patients to maintain proper levels of insulin production when required. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient. Type 1 diabetes (T1D) patients are required to take insulin (e.g., via injections or infusion) to move glucose from the bloodstream because their bodies generally cannot produce insulin. Type 2 diabetes (T2D) patients generally can produce insulin but their bodies cannot use the insulin properly to maintain blood glucose levels within medically acceptable ranges. In contrast to people with T1D, the majority of those with T2D usually do not require daily doses of insulin to survive. Many people are able to manage their condition through a healthy diet and increased physical activity or oral medication. However, if they are unable to regulate their blood glucose levels, they will be prescribed insulin. For example, there are an estimated 6.2 million Type 2 diabetes patients (e.g., in the United States, Western Europe and Canada) taking multiple-daily-injections (MDI) which consist of a 24-hour basal insulin and a short acting rapid insulin that is taken at mealtimes for glycemic management control.

For the treatment of Type 1 diabetes (T1D) and sometimes Type 2 diabetes (T2D), there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates to more closely match the functions and behavior of a properly operating pancreas of a nondiabetic person that produces the required insulin, and the insulin pump can help the diabetic patient maintain his/her blood glucose level within target ranges based on the diabetic patient's individual needs. Infusion pump therapy requires an infusion cannula, typically in the form of an infusion needle or a flexible catheter, that pierces the diabetic patient's skin and through which infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life. For example, many of the T2D patients who are prescribed insulin therapy can be expected to convert from injections to infusion therapy due to an unmet clinical need for improved control. That is, a significant number of the T2D patients who take multiple-daily-injections (MDI) are not achieving target glucose control or not adhering sufficiently to their prescribed insulin therapy.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps use a disposable component, typically referred to as an infusion set, tubing set or pump set, which conveys the insulin from a reservoir within the pump into the skin of the user. The infusion set includes a pump connector, a length of tubing, and a hub or base from which a cannula, in the form of a hollow metal infusion needle or flexible plastic catheter, extends. The base typically has an adhesive that retains the base on the skin surface during use. The cannula can be inserted onto the skin manually or with the aid of a manual or automatic insertion device. The insertion device may be a separate unit employed by the user.

Another type of insulin pump is a patch pump. Unlike a conventional infusion pump and infusion set combination, a patch pump is an integrated device that combines most or all of the fluidic components in a single housing. Generally, the housing is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®, while others are completely self-contained. Such patch pumps are replaced on a frequent basis, such as every three days, or when the insulin reservoir is exhausted. Otherwise, complications may occur, such as restriction in the cannula or the infusion site.

As patch pumps are designed to be a self-contained unit that is worn by the patient, preferably, the patch pump is small, so that it does not interfere with the activities of the user. Thus, to minimize discomfort to the user, it is preferable to minimize the overall thickness of the patch pump. However, to minimize the thickness of the patch pump, the size of its constituent parts and the number of parts should be reduced as much as possible.

In current patch pump designs, tubes, such as plastic tubes, are employed as fluid pathways to route fluid flow from one internal component to another. The use of multiple tubes can create multiple flow paths to transfer medicament. For example, there can be two flow paths connected to a reservoir. One flow path fills the reservoir with medicament and another flow path routes the medicament from the reservoir to various internal components in the patch pump. The use of tubes can increase cost and can result in additional complexity during device assembly. For example, such device assembly includes connecting the tubes, which adds steps to the assembly process. In addition, preventing leaks from such connections can give rise to additional challenges.

Accordingly, a need exists for an improved fluid path design for use in a limited space environment, such as in a patch pump device, which can cost-effectively transport medicament, while minimizing or reducing the overall size and complexity of the device.

SUMMARY OF EMBODIMENTS OF THE INVENTION

It is an aspect of the present invention to provide a patch pump in which a filling member is substantially simultaneously in fluid communication with a reservoir and a pump to effectively and efficiently administer the medicament to the patient.

The foregoing and/or other aspects of the present invention can be achieved by providing a filling member in a medicament delivery device, the filling member comprising a first conduit that fluidly communicates with a reservoir, and a second conduit that fluidly communicates with a pump and with the first conduit, wherein the filling member provides two-way medicament flow that (1) enters the reservoir via the first conduit, (2) exits the reservoir into the first conduit and the second conduit, and (3) exits the second conduit to the pump.

The foregoing and/or other aspects of the present invention can also be achieved by providing a device for delivering medicament into skin of a patient, the device comprising a filling member including a septum cavity for housing a septum, a first conduit that fluidly communicates with a reservoir, and a second conduit that fluidly communicates with the first conduit and a pump, wherein the filling member provides two-way medicament flow that (1) enters the reservoir via the first conduit, (2) exits the reservoir into the first conduit and the second conduit, and (3) exits the second conduit to the pump.

Moreover, the foregoing and/or other aspects of the present invention can be further achieved by providing a medicament delivery method comprising inserting at least a portion of a medicament container through a septum of a filling member, transporting medicament from the medicament container into a conduit of the filling member to fill a reservoir, removing the medicament container from the septum, transporting the medicament from the reservoir into the conduit of the filling member, and transporting the medicament to exit the filling member.

The foregoing and/or other aspects of the present invention can also be further achieved by providing a medicament filling method comprising inserting at least a portion of a medicament container into a septum of a filling member, transporting medicament from the medicament container to a reservoir via a first conduit of the filling member, and to a pump via a second conduit of the filling member, and removing the medicament container from the septum.

Additionally, the foregoing and/or other aspects of the present invention can be achieved by providing a medicament delivery device comprising a pump disposed in the device, wherein the pump controls flow of medicament to a patient, a filling member including a septum adapted to provide access to an interior of the filling member via penetration therethrough, a septum cavity for housing the septum, a first conduit that fluidly communicates with a reservoir, and a second conduit that fluidly communicates with the first conduit and the pump, and a delivery cannula that receives the medicament from the pump and delivers the medicament into skin of the patient, wherein the filling member provides two-way medicament flow that: (1) enters the reservoir via the first conduit, (2) exits the reservoir into the first conduit and the second conduit, and (3) exits to the pump.

The foregoing and/or other aspects of the present invention can also be further achieved by providing a device for delivering medicament into skin of a patient, the device comprising a housing including a base with a filling opening, the housing including a pump that controls flow of the medicament to a patient, a reservoir that houses the medicament, a filling member that transports the medicament, and a septum disposed between the filling opening and the filling member, the septum sealing the filling opening, wherein the filling member includes a region adjacent to the septum, the region being in fluid communication with both the reservoir and the pump.

Additional and/or other aspects and advantages of the present invention will be set forth in the description that follows, or will be apparent from the description, or may be learned by practice of the invention. The present invention may comprise delivery devices and methods for forming and operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, of which.

DETAILED DESCRIPTION OF EMBODIMENTS OF THE PRESENT INVENTION

Figure 1:
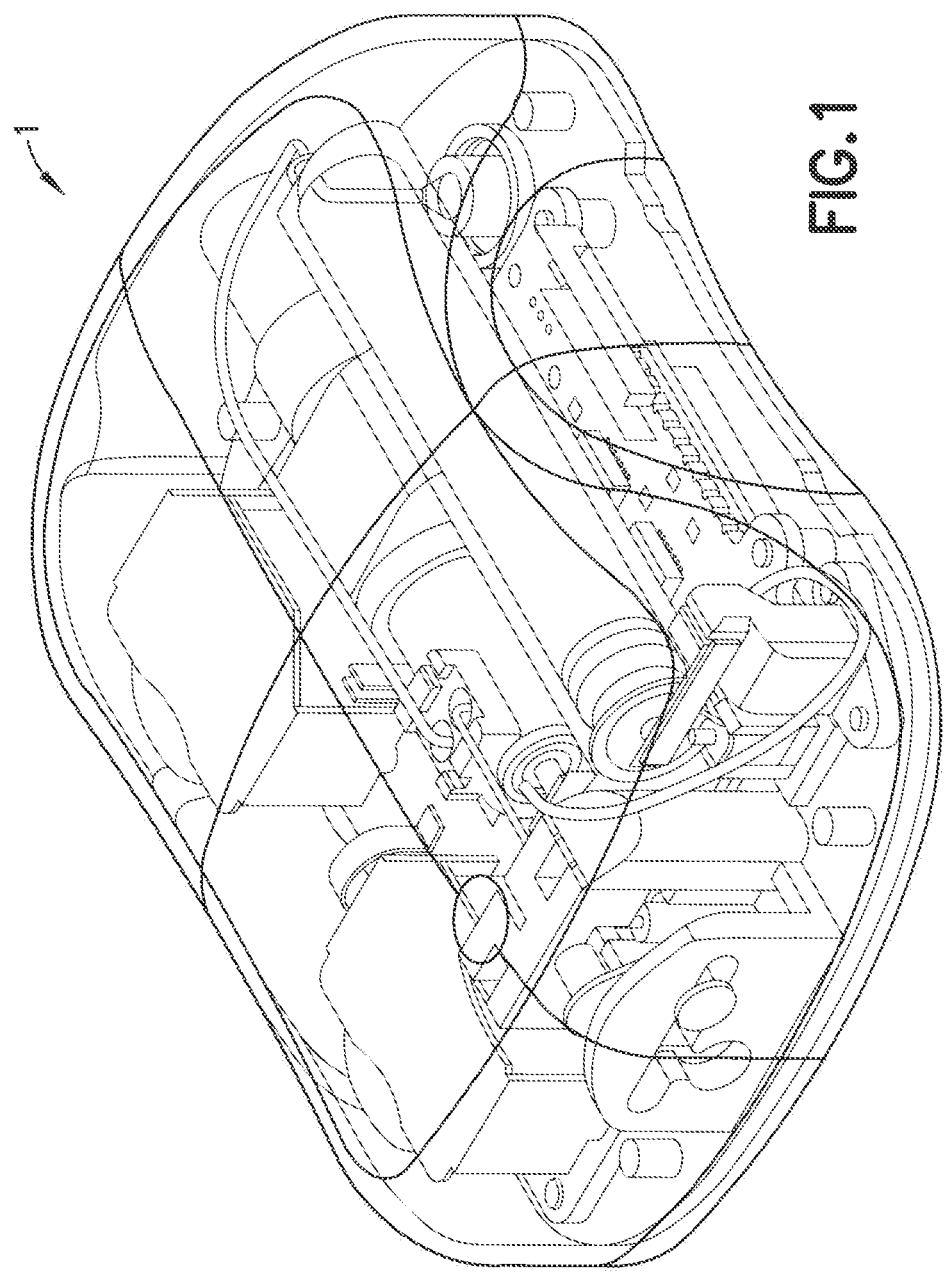
FIG. 1 is a perspective view of a patch pump constructed in accordance with an illustrative embodiment of the present invention in which a cover is shown as being translucent for clarity.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The illustrative embodiments are described with reference to diabetes management using insulin therapy. It is to be understood that these illustrative embodiments can be used with different drug therapies and regimens to treat other physiological conditions than diabetes using different medicaments than insulin.

Figure 2:
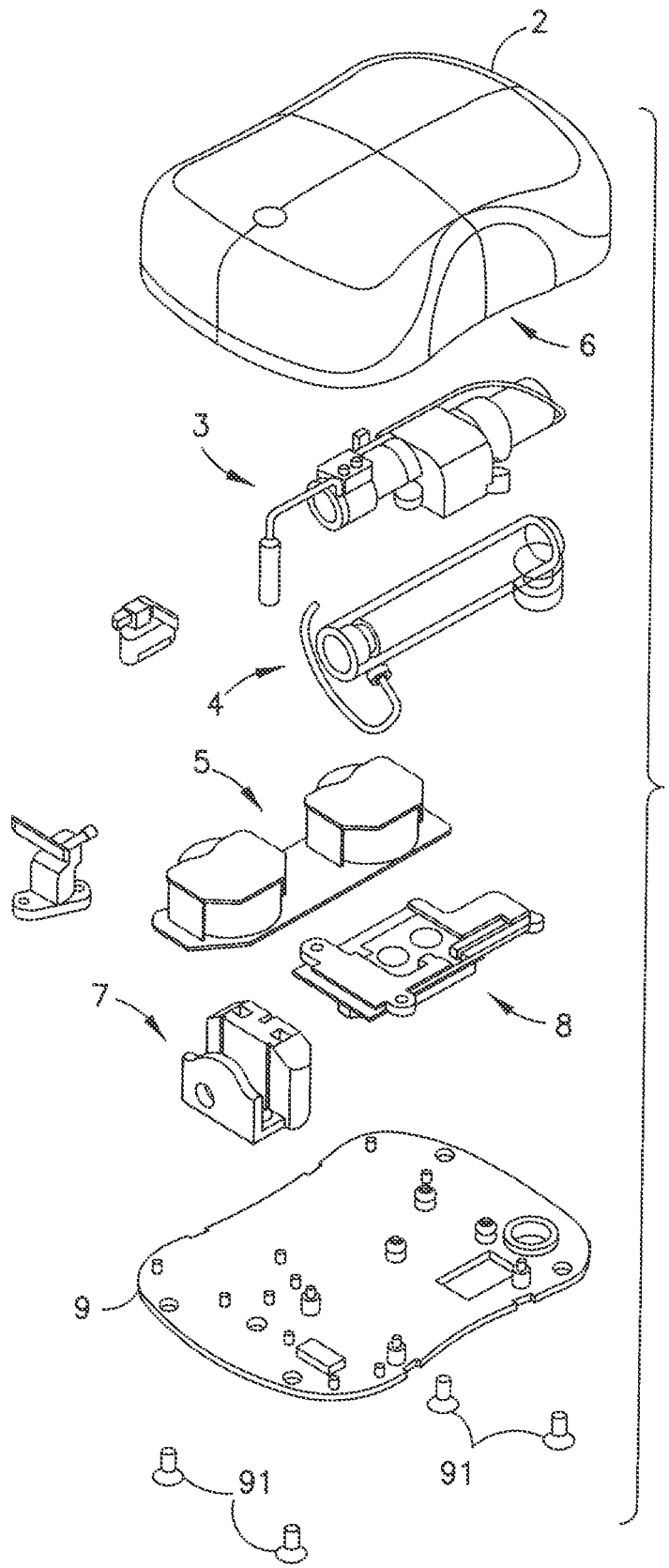
FIG. 2 is an exploded view of various components of the patch pump of FIG. 1.

FIG. 1 is a perspective view of an exemplary embodiment of a medicine delivery device comprising a patch pump 1 according to an exemplary embodiment of the invention. The patch pump 1 is illustrated with a see-through cover for clarity and illustrates various components that are assembled to form the patch pump 1. FIG. 2 is an exploded view of the various components of the patch pump of FIG. 1, illustrated with a main cover 2. The various components of the patch pump 1 may include: a reservoir 4 for storing insulin; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a pair of dose buttons 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

Figure 3:
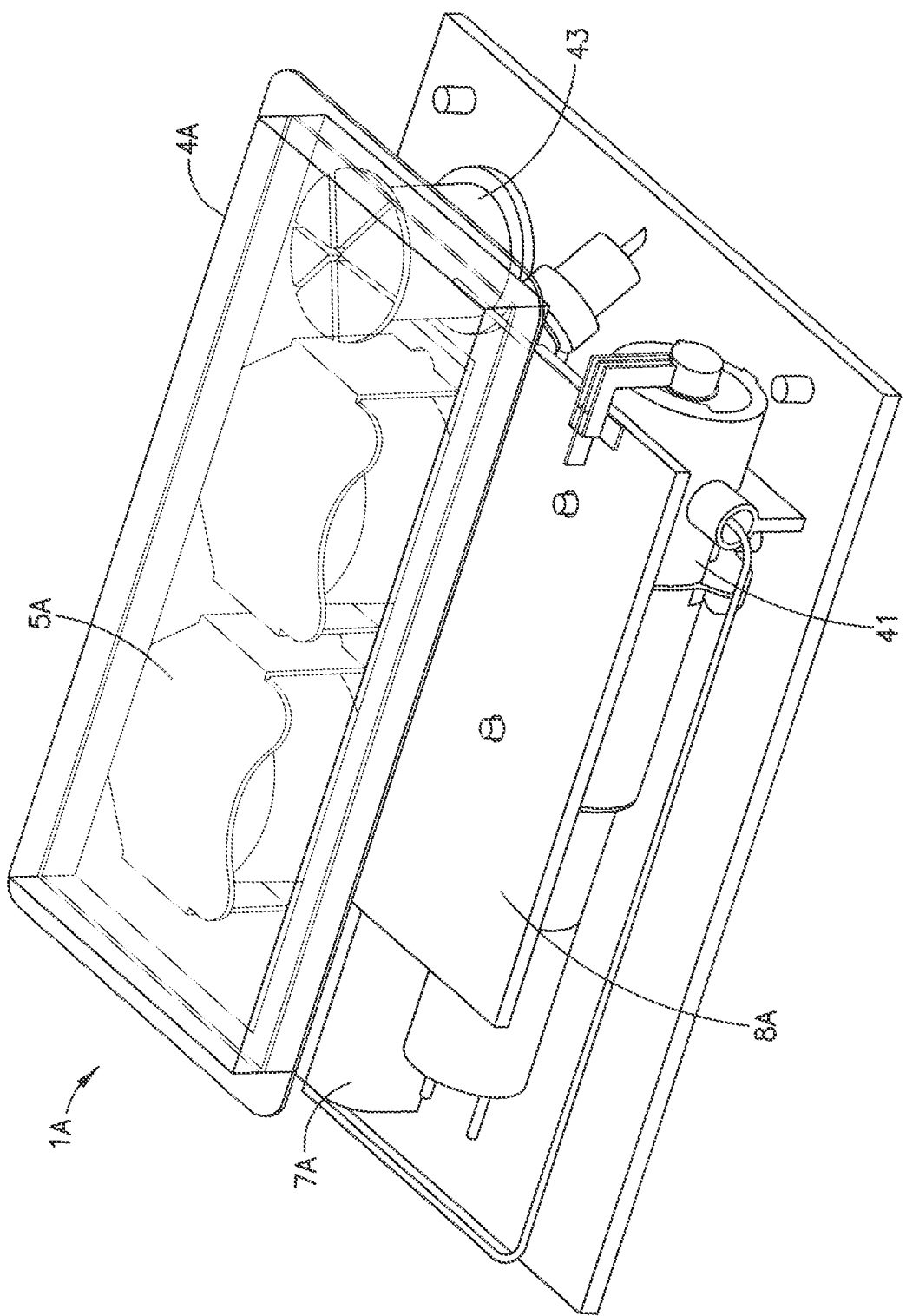
FIG. 3 is a perspective view of an alternative design for a patch pump having a flexible reservoir, illustrated without a cover, in accordance with an illustrative embodiment of the present invention

FIG. 3 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir filling member 43 for receiving a refill syringe 45 to fill the reservoir 4A.

Figure 4:
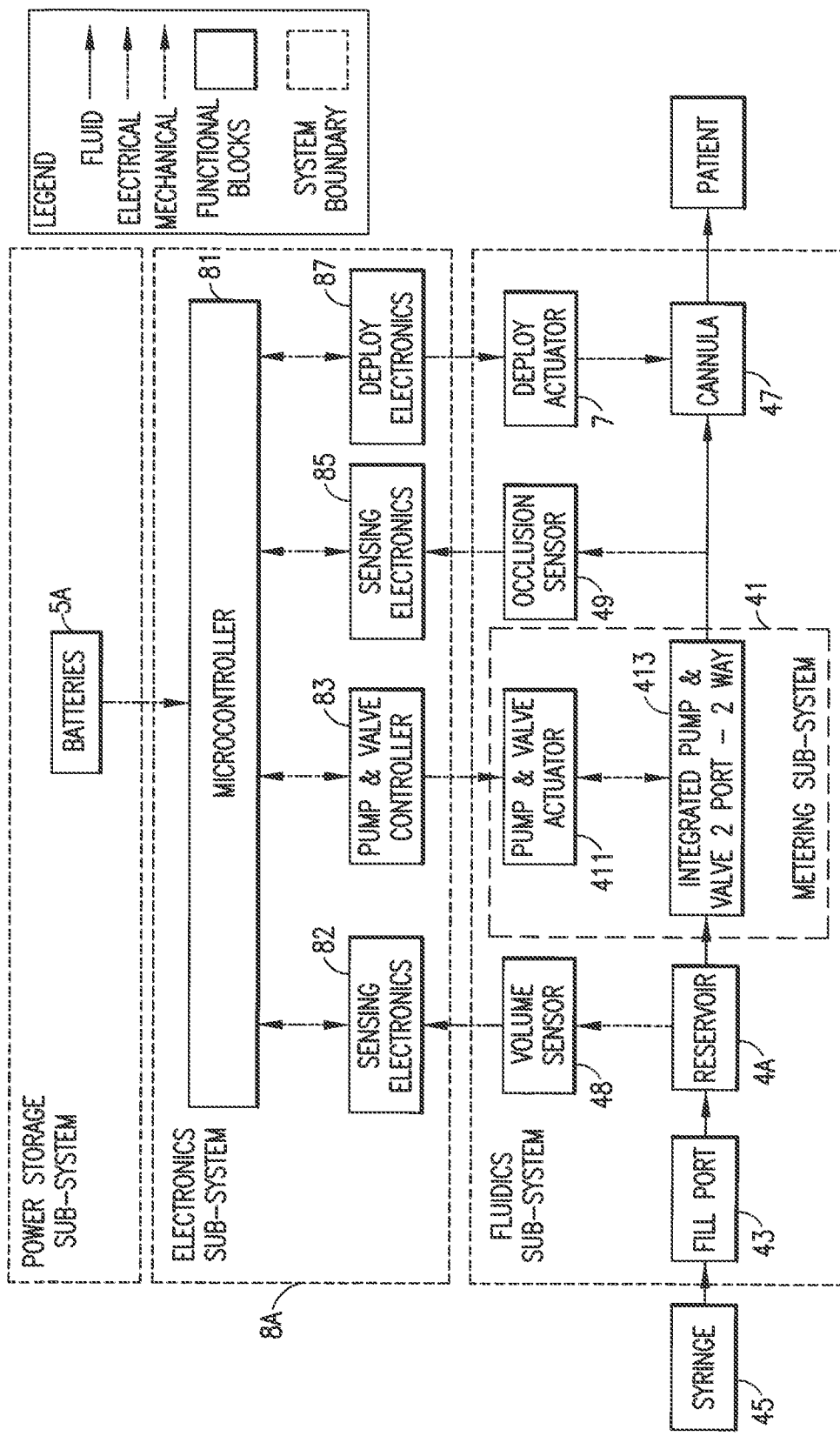
FIG. 4 is a perspective view of a patch-pump fluidic architecture and metering sub-system diagram of the patch pump of FIG. 3.

FIG. 4 is a patch-pump fluidic architecture and metering sub-system diagram of the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87, which control the actuation of the patch pump 1A. The patch pump 1A includes a fluidics sub-system that may include a reservoir 4A, volume sensor 48 for the reservoir 4A, a reservoir filling member 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 1 and 2 is the same or similar to that which is illustrated in FIG. 4.

Figure 5:
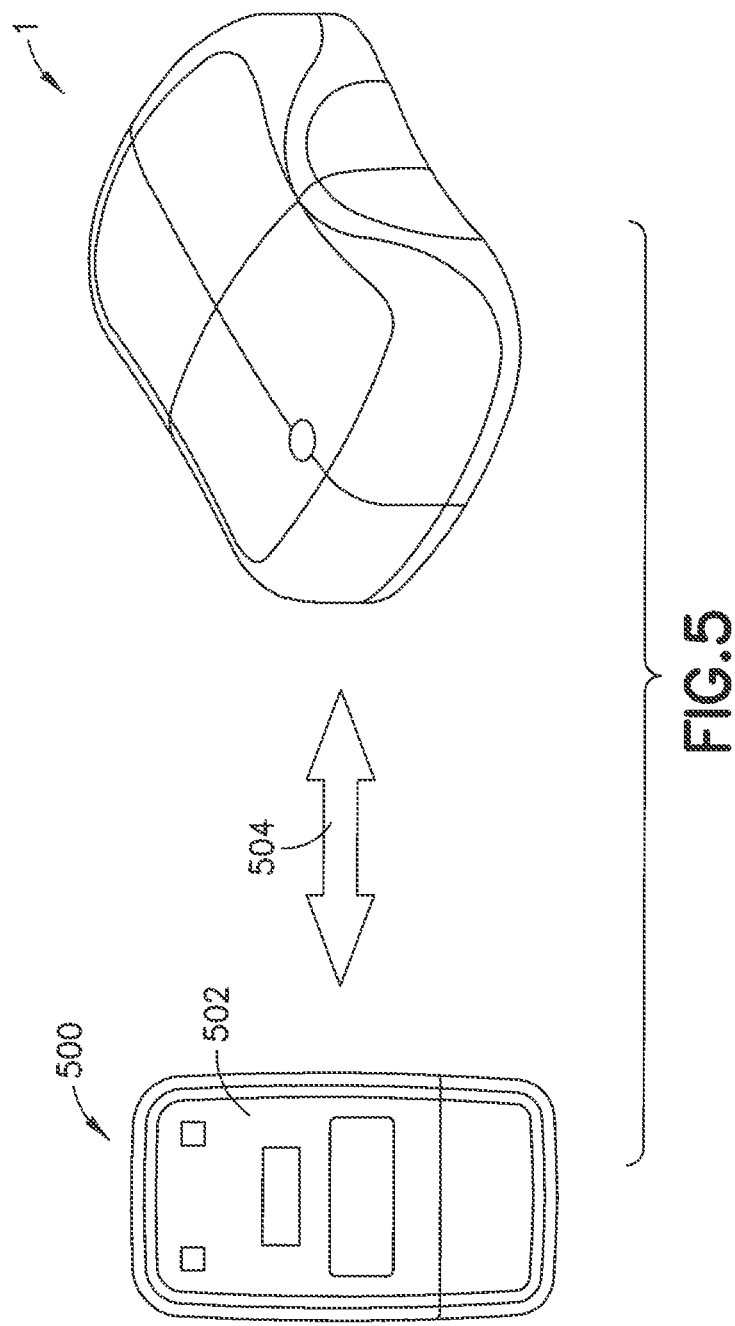
FIG. 5 illustrates an example wireless remote controller for controlling the operation of a medicine delivery device such as, for example, a patch pump, in accordance with an illustrative embodiment of the present invention.

With reference to FIG. 5, the wearable medical delivery device (e.g., insulin delivery device (IDD) such as patch pump 1 is operable in conjunction with a remote controller that preferably communicates wirelessly with the pump 1 and is hereinafter referred to as the wireless controller (WC) 500. The WC can comprise a graphical user interface (GUI) display 502 for providing a user visual information about the operation of the patch pump 1 such as, for example, configuration settings, an indication when a wireless connection to the patch pump is successful, and a visual indication when a dose is being delivered, among other display operations. The GUI display 502 can include a touchscreen display that is programmed to allow a user to provide touch inputs such as a swipe to unlock, swipe to confirm a request to deliver a bolus, and selection of confirmation or settings buttons, among other user interface operations.

The WC 500 can communicate with the delivery device (e.g., patch pump 1) using any one or more of a number of communication interfaces 504. For example, a near field radiation interface is provided to synchronize the timing of the WC and patch pump 1 to facilitate pairing upon start up. Another interface can be provided for wireless communication between the WC and the patch pump 1 that employs a standard BlueTooth Low Energy (BLE) layer, as well as Transport and Application layers. Non-limiting examples of Application layer commands include priming, delivering basal dose, delivering bolus dose, cancelling insulin delivery, checking patch pump 1 status, deactivating the patch pump 1, and patch pump 1 status or information reply.

Figure 6:
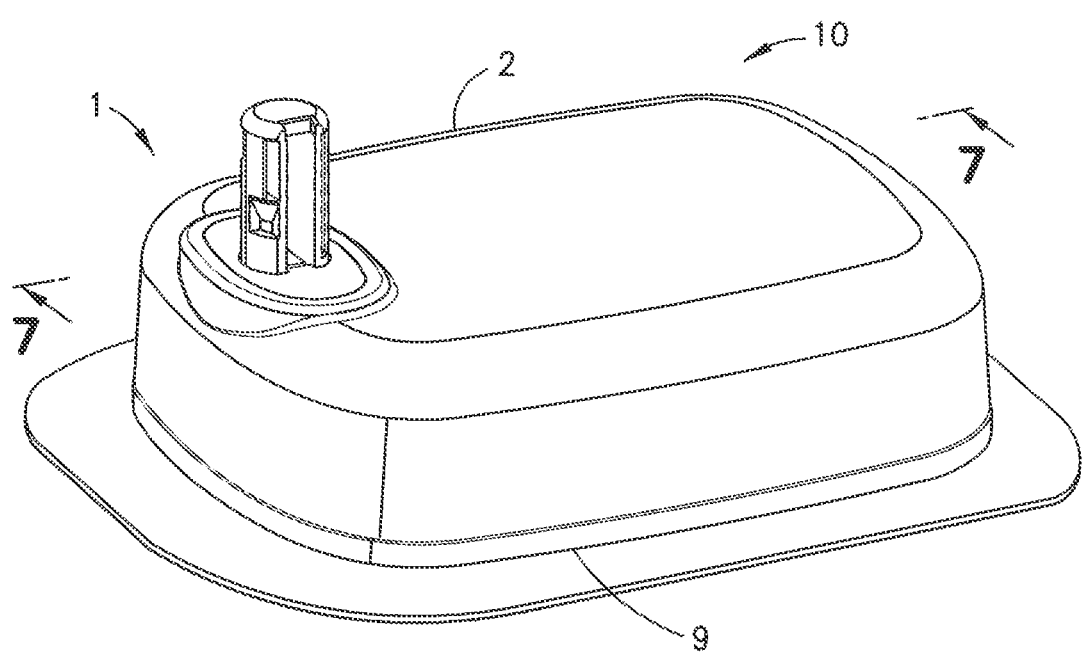
FIG. 6 is a perspective view of a patch pump in accordance with an illustrative embodiment of the present invention.

FIG. 6 is a perspective view of a patch pump 1 according to an exemplary embodiment of the present invention. The patch pump 1 has a housing 10, which includes a main cover 2 liquid sealed or, preferably, hermetically sealed to a base 9. The base 9 carries various components as described below in detail. The hermetic seal prevents fluid ingress and prevents other particles from passing the seal. Embodiments of the patch pump 1 also include a vent or a vent membrane along with a sealing method described herein to provide pressure equalization.

Embodiments of the seal include, for example, a liquid-tight seal, an O-ring seal or another mechanical seal, a gasket, an elastomer, a heat seal, an ultra-sonically welded seal, a laser weld, chemical joining, an adhesive, a solvent weld, or an adhesive weld. Laser welding is the preferred sealing method because when laser welding is properly performed, a seamless fully hermetic seal is formed. The vent or the vent membrane continues to have the functional purpose of equalizing internal pressure and providing a sterile environment. One skilled in the art will appreciate that other seals can be used without departing from the scope of the present invention.

Figure 7:
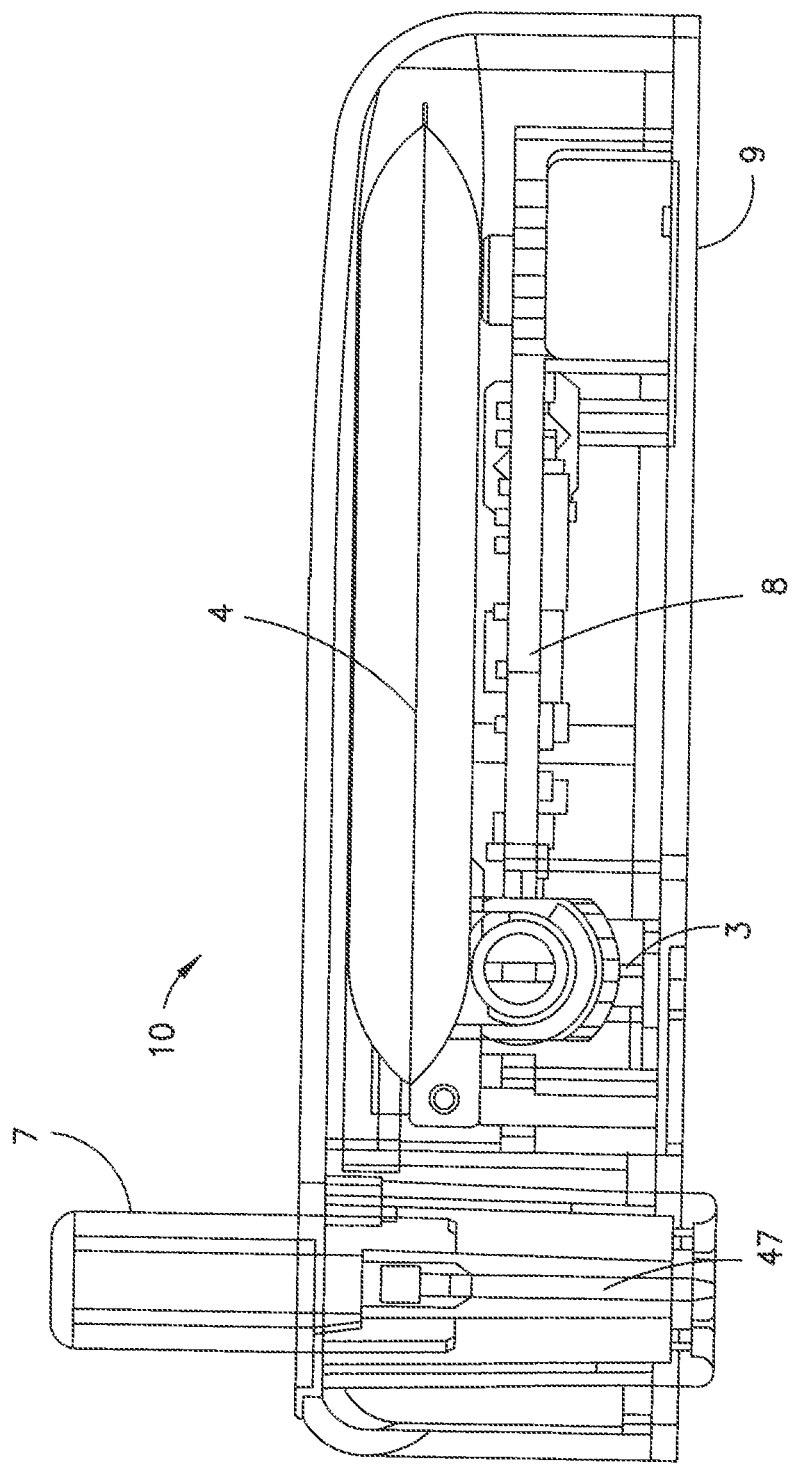
FIG. 7 is a cross-sectional view of FIG. 6 taken along line 7-7 of FIG. 6.

FIG. 7 is a cross-sectional view of the patch pump 1 illustrating various internal components. The main cover 2 and the base 9 house the components of the patch pump 1. According to one embodiment, the patch pump 1 preferably includes a reservoir 4 for storing medicament (such as insulin) and a pump 3 for pumping the medicament to exit the reservoir 4. The patch pump 1 also preferably includes electronics 8 for programming and operating the patch pump 1, and an insertion mechanism 7 for inserting a cannula 47 into a skin of the patient to deliver medicament. Examples of the electronics 8 include semiconductor chips, controllers, diodes, antennas, coils, batteries, discrete components (resistors and capacitors, for example) and circuit boards used to operate and control the patch pump 1 and operate the pump 1 in conjunction with the WC 500.

Figure 8:
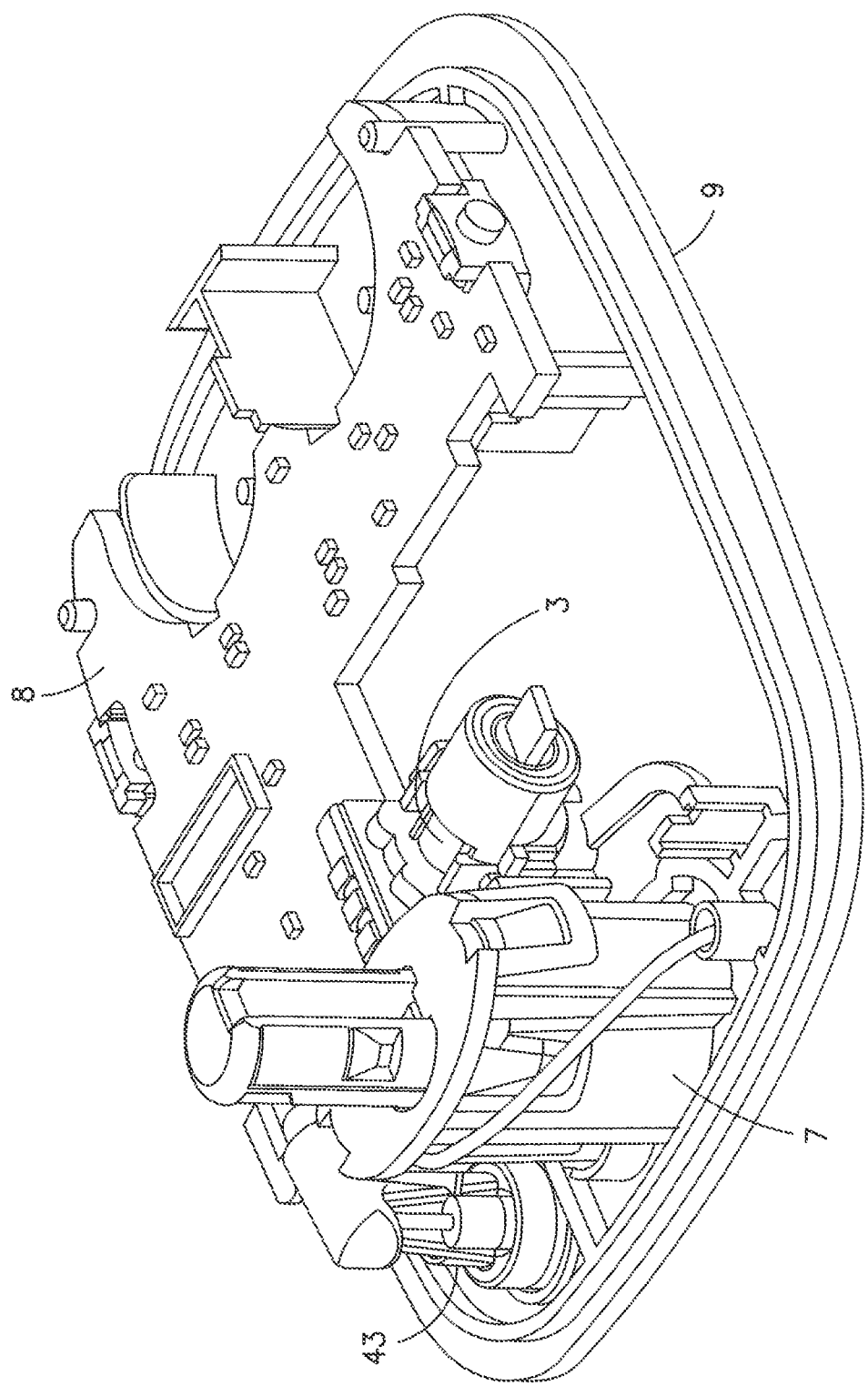
FIG. 8 is a perspective view of the patch pump of FIG. 6, omitting a cover and a reservoir.

FIG. 8 illustrates some of the main components of the patch pump 1 in a perspective view with the main cover 2 and the reservoir 4 removed for clarity. According to one embodiment, a filling member 43 is a conduit for supplying the medicament to the reservoir 4. In some embodiments, the filling member 43 includes a portion that serves as part of the flow path for medicament exiting the reservoir 4. The filling member 43 and the reservoir 4 will be described in further detail below.

Figure 9:
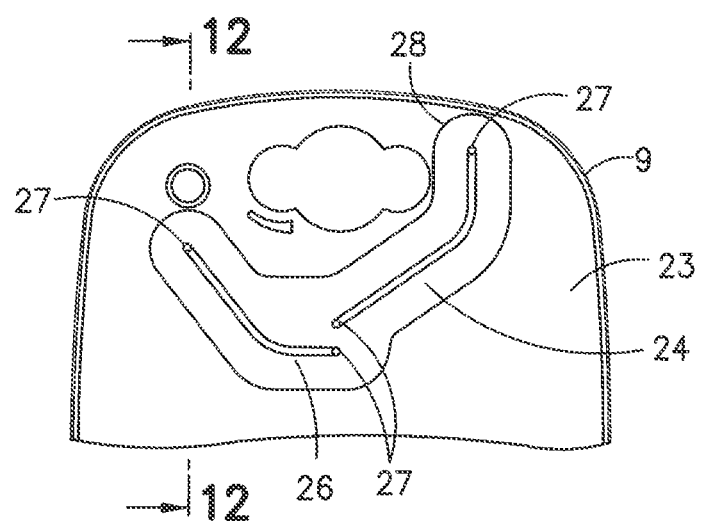
FIG. 9 is a bottom view of the patch pump of FIG. 6.

FIG. 9 illustrates a bottom surface 23 of the base 9 of the patch pump 1. The base 9 is preferably composed of a stiff material such as a thermoplastic resin (e.g., LG Chem Ltd. product no. TR-558ai MABS (clarified)) or similar material that can support and be configured with various components of the pump 1 and recessed channels 24, 26 as shown, for example, in FIGS. 8 and 9, and which favorably reacts with laser welding and insulin upon contact. The base 9 is preferably clear and laser transmissive. During use, the bottom surface 23 is oriented toward the skin of the patient. In some embodiments, the bottom surface 23 can include adhesive that removably attaches the base 9 to the skin of the patient. Alternatively, an adhesive pad adheres to both the bottom surface 23 and the skin of the patient. Preferably, 3M™ medical tape (e.g., product no. 1776) is the adhesive used, although various types of known industry adhesives can be used. However, the adhesive is carefully selected to ensure compatibility with human skin to prevent undesired reactions. Also, compatibility of the adhesive and the insulin is considered in case that the adhesive and the insulin accidentally mix. The adhesive or adhesive pad are also placed over a fluid channel cover 28 covering first and second fluid channels 24, 26.

The bottom surface 23 of the base 9 includes first and second fluid channels 24, 26. The first and second fluid channels 24, 26 provide fluid pathways between various components in the patch pump 1. According to one embodiment, the first and second fluid channels 24, 26 advantageously establish fluid communication between various components such as the reservoir 4, the filling member 43, the pump 3, and the insertion mechanism 7.

Preferably, the first and second fluid channels 24, 26 are recessed from the bottom surface 23 or etched or inscribed into the bottom surface 23 of the base 9. As examples, the first and second channels 24, 26 are formed by a molding process, such as injection molding, or by a cutting process, such as milling. In other embodiments, the first and second fluid channels 24, 26 are disposed on the main cover 2, or on the base 9 within the interior of the patch pump 1. Similar fluid channels can be positioned in a plurality of locations in embodiments of the device.

According to one embodiment as illustrated in FIG. 9, the first and second fluid channels 24, 26 are encapsulated by a fluid channel cover 28 which is illustrated as being transparent for clarity. One skilled in the art will appreciate that the opacity of the fluid channel cover 28 or other portions of the device can vary without departing from the scope of the present invention. The fluid channel cover 28 is, for example, clear film, foil, a flexible sheet/film or a semi-rigid/rigid part made of any suitable material.

According to one embodiment, the film channel cover 28 is composed of foil available from Oliver-Tolas Healthcare Packaging (e.g., TPC-0777A foil) or similar material. Preferably, the film channel cover 28 is composed of Oliver-Tolas Healthcare Packaging product no. IDT-6187 clear film or similar material and is heat sealed or heat staked to the bottom surface 22 of the base 9 to embed the first and second fluid channels 24, 26. Laser welding, for example, applies laser light through the clear film to fix the film channel cover 28 to the bottom surface 22 of the base 9. The fluid channel cover 28 is sealed to the base 9 via any of the processing methods described above. The sealed fluid channel cover 28 encloses and protects the medicament from any contamination while travelling through the first and second fluid channels 24, 26. Laser welding is advantageous because a laser can straddle the channel edge of the fluid channels 224, 26 during the welding process and join (or adhere) the film to the base 9 in areas that are closer to the channel edges than other methods.

Figure 10:
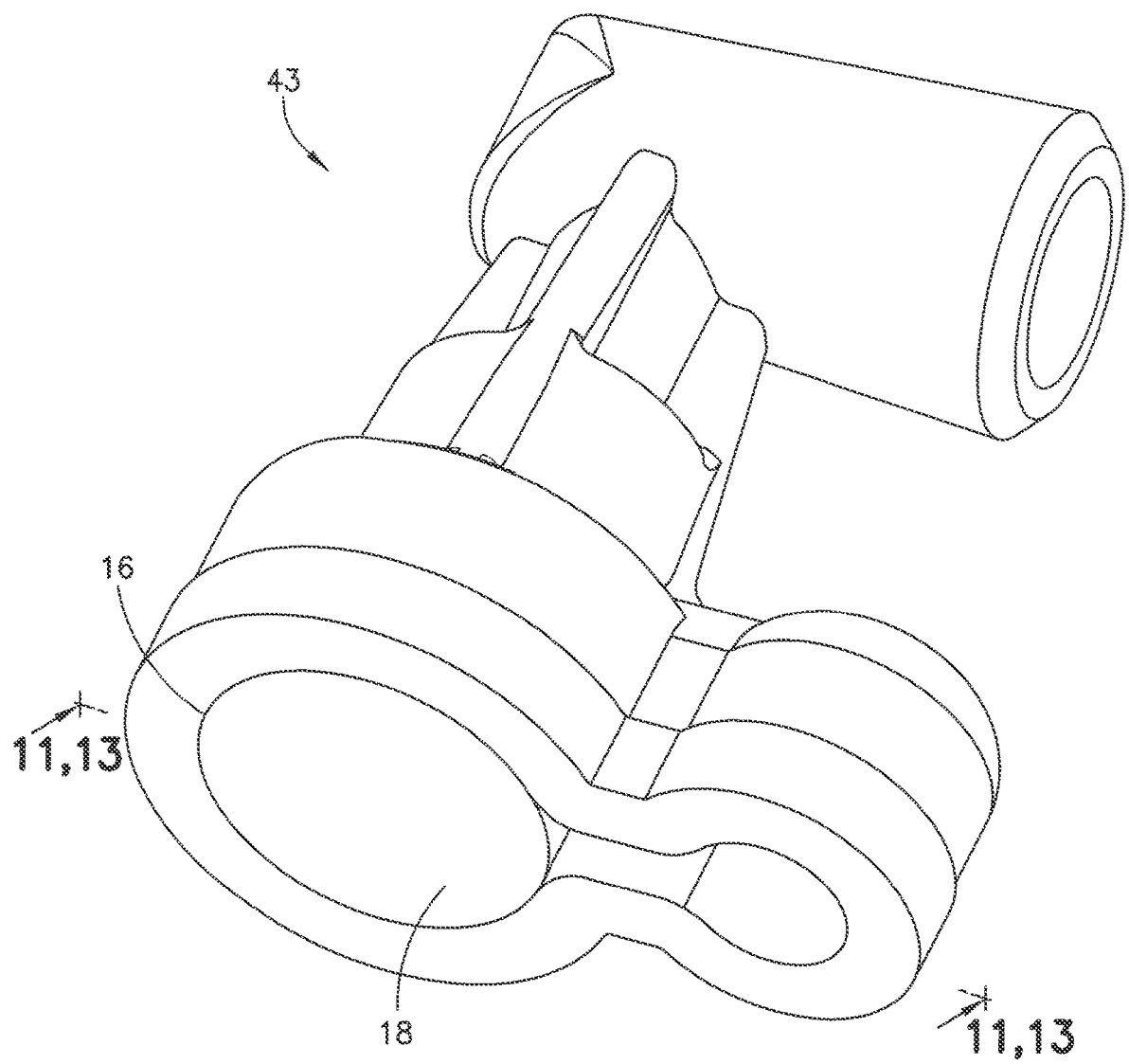
FIG. 10 is a perspective view of a filling member in the patch pump of FIG. 8, in accordance with an illustrative embodiment of the present invention.

FIG. 10 is a perspective view of a filling member 43 in the patch pump of FIG. 8. According to one embodiment, the filling member 43 includes a septum 18 disposed in a septum cavity 16. As described below, the septum 18 is adapted to provide access to an interior of the filling member 43. Specifically, a user pierces the septum 18 with a portion of a medicament container, such as a needle of a syringe, to fluidly communicate with the various passageways in the filling member 43.

Figure 11:
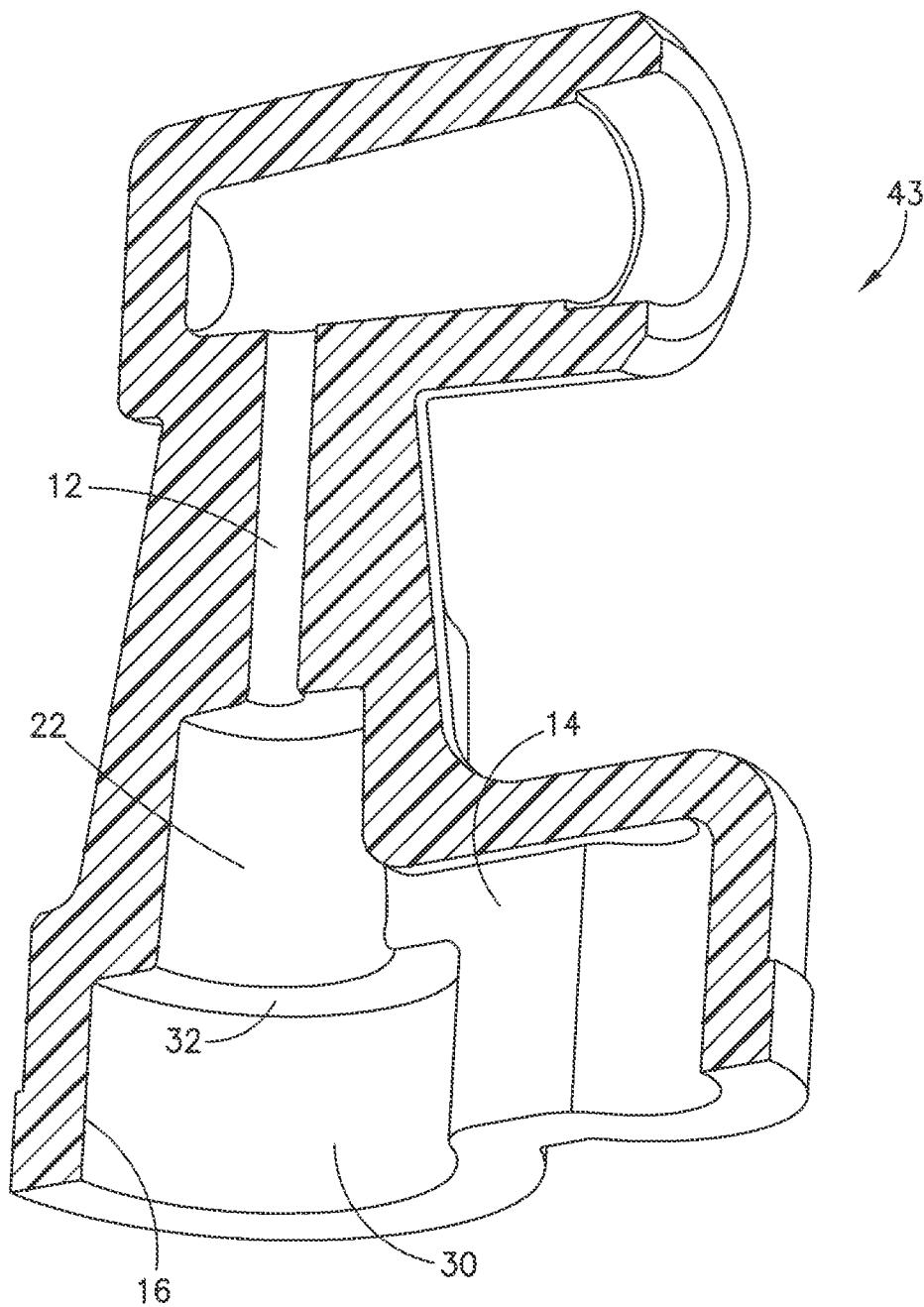
FIG. 11 is a cross-sectional perspective view of the filling member taken along line 11-11 of FIG. 10.

FIG. 11 is a cross-sectional perspective view of the filling member taken along line 11-11 of FIG. 10. Although the filling member 43 can be formed of multiple, joined parts, the filling member 43 is preferably injection molded and integrally formed as a unitary structure. Alternatively, the filling member 43 can be a casting that is integrally formed as a unitary structure and subsequently machined to precision. As another alternative, the filling member can be milled. The unitary structure of the filling member 43 advantageously reduces the number of components, improves subassembly processing, and simplifies the design of the patch pump 1.

According to one embodiment, the filling member 43 is clear. Preferably, the filling member 43 is a carbon black based fill port composed of Lustran 348 with PolyOne CC1021.3952 Carbon Black in 3% let down ratio (LDR) or similar material. Alternately, the filling member 43 is LG Chem Ltd. product no. TR-558ai MARS (clarified). These materials advantageously provide less stringent number of critical to qualities (CTQ) tolerances, thus resulting in improved manufacturability. Additionally, these materials include a laser welding additive that supports and facilitates laser welding.

Figure 12:
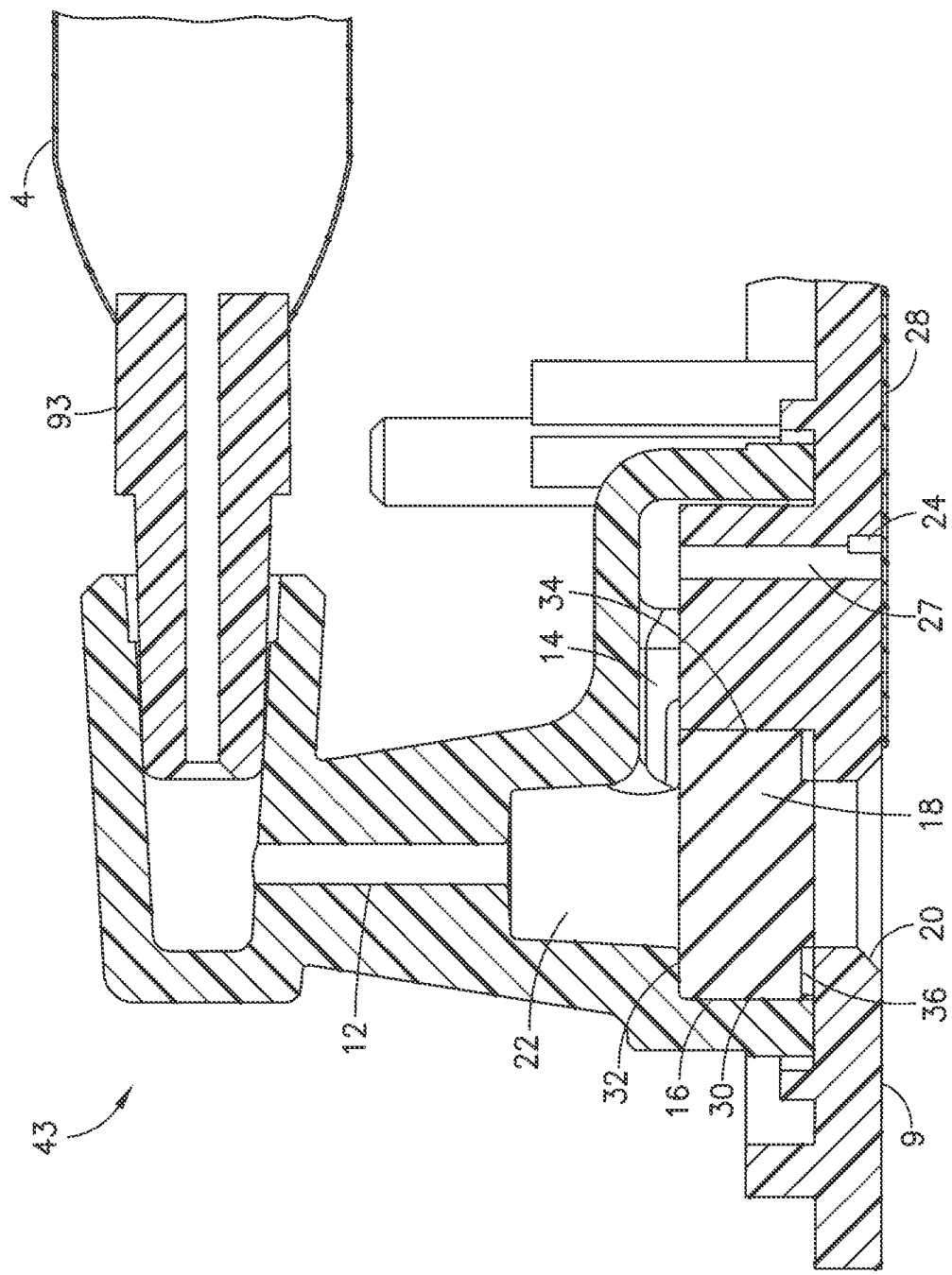
FIG. 12 is a partial cross-sectional view of the filling member in the patch pump of FIG. 6 taken along line 12-12 of FIG. 9.

FIG. 12 is a partial cross-sectional view of the filling member 43 installed within the patch pump 1. The filling member 43 is sealed to the base 9 in a liquid-tight manner or hermetically sealed. According to one embodiment, the sealing interface between the filling member 43 and the base 9 includes adhesives, for example, adhesive material 1162-M or Loctite 3922 or similar material. It is desirable for the adhesive not to mix with the medicament because, for example, the insulin concentration is reduced by 5%-15%. Adhesive contamination into the medicament can be detrimental to the health and safety of the patient receiving the medicament. In accordance with one embodiment of the present invention, the filling member 43 is press fit to a tube 44A configured with or without a receptacle 93, thereby connecting to the reservoir 4. Illustrative reservoir connections are described below in connection with FIGS. 16-22.

Alternatively, other sealing arrangements can include a mechanical seal, a heat seal, an ultra-sonically welded seal, a laser weld, chemical joining, a solvent weld, or an adhesive weld. Some examples of the mechanical seal include O-rings and gaskets. For the reasons described below, the sealing interface between the filling member 43 and the base 9 prevents contamination of the medicament.

Preferably, the filling member 43 is bonded to the base 9 by laser welding. The filling member 43 is configured to include additives for laser absorbency. Laser welding advantageously avoids the mixing of insulin and adhesive. Moreover, laser welding advantageously provides flexibility in positioning the filling member 43 in the base 9. Laser welding also regulates the compression of the septum 18 by controlling the melt collapse (described below) of the filling member 43. Specifically, under a standard interference fit, the septum 18 is compressed radially and axially. However, laser welding can limit the pressure on the septum 18 to solely axial compression. The filling member 43 collapses a controlled amount during laser welding to set the proper septum compression while considering all part and process tolerances. For example, the septum 18 is compressed by approximately 10% compared to a nominal axial length, whereas the septum 18 is very slightly compressed radially when assembled so that the septum 18 does not fall out during assembly.

As shown in FIG. 12, the base 9 preferably includes a filling opening 20. According to one embodiment, the filling opening 20 is a counter-sunk through-hole that contacts the septum 18. One skilled in the art will appreciate that the through-hole could be counter-bored, straight-sided, or have some other shape without departing from the scope of the present invention.

Figure 13:
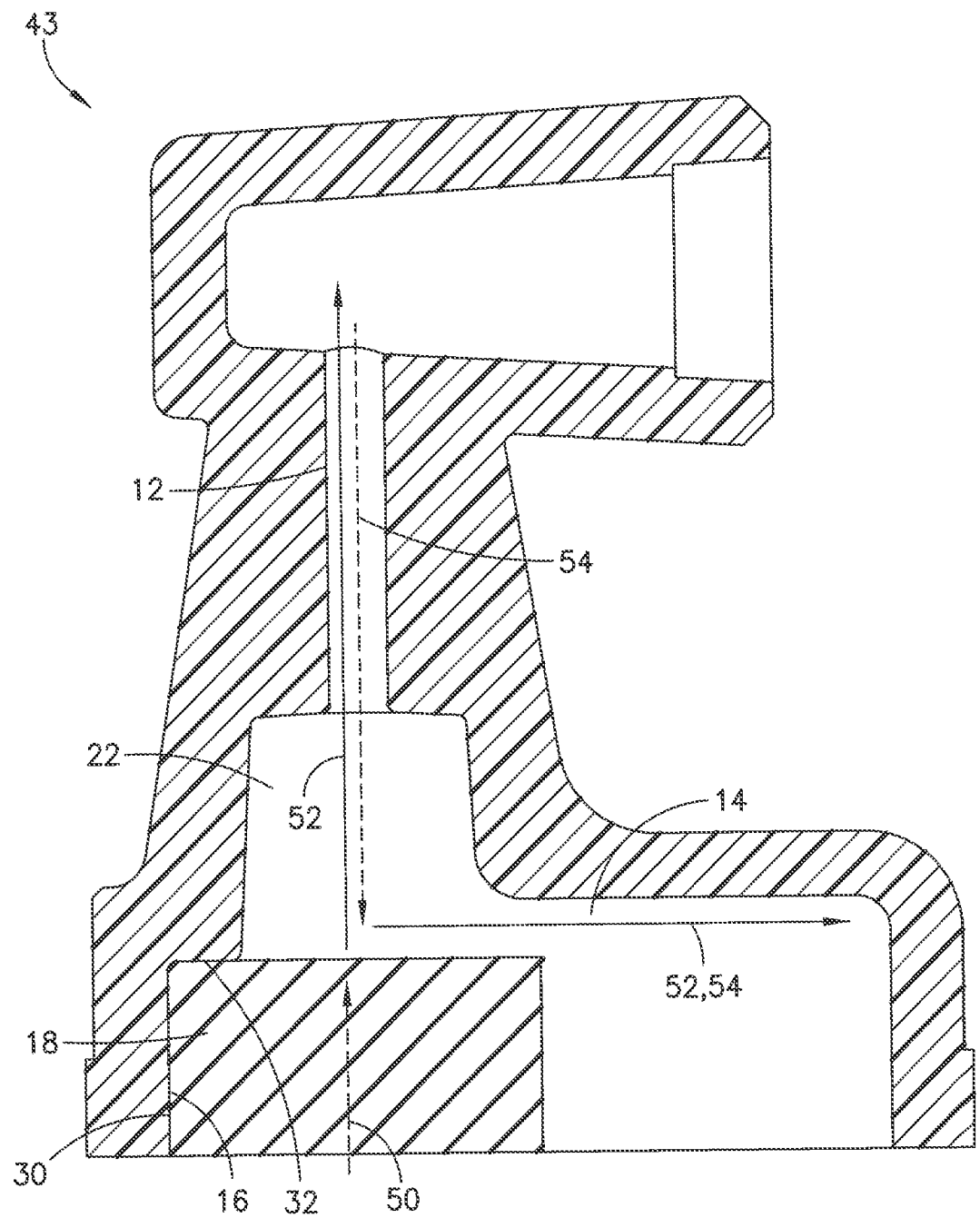
FIG. 13 is a cross-sectional view of the filling member and a septum taken along line 13-13 of FIG. 10.

FIG. 13 illustrates a cross-sectional view of the filling member 43 and the septum 18 taken along line 13-13 of FIG. 10. As illustrated in FIGS. 12 and 13, the septum 18 is housed in a septum cavity 16 at a position above and adjacent to the filling opening 20. The septum cavity 16 is defined by walls 30, 32 in the filling member 43 and walls 34, 36 in the base 9. Specifically, the base 9, as illustrated in FIG. 12, forms a bottom surface 36 and a circumferential, side surface 34 of the septum cavity 16. The filling member 43, as illustrated in FIG. 13, forms a top surface 32 and an opposing circumferential, side surface 30 of the septum cavity 16. As a result, the septum 18 is positioned between the base 9 and the filling member 43 and seals the filling opening 20.

Preferably, the septum 18 is composed of a material known in the industry as Kokoku Rubber Inc. product no. A1N-4509-M 40A durometer or similar material. According to one embodiment, a round septum 18 is held by the filling member 43 by the use of an adhesive. The round septum design provides ease in assembly. According to another illustrative embodiment, a keyhole septum 18 is press fitted into the base 9 and the filling member 43 to prevent adhesive from mixing with the insulin. The keyhole septum design provides a simpler configuration and improved manufacturability compared to the round septum design.

When the filling member 43 is sealed to the base 9 during assembly, the septum 18 is advantageously compressed in the septum cavity 16 to seal the filling member 43 at the filling opening 20. In the round septum design, the septum 18 is compressed a predetermined amount both axially and radially with respect to the centerline of the filling opening 20 to ensure proper sealing. Specifically, the septum 18 is compressed between the top and bottom surfaces 32, 36 of the septum cavity 16 in an axial direction via the filling member 43 and the base 9. Additionally, the septum 18 is compressed radially between the circumferential side surfaces 30, 34 of the septum cavity 16 via the filling member 43 and the base 9.

The use of the septum 18 in the septum cavity 16 of the filling member 43 provides several benefits. For example, the septum 18 advantageously seals the filling member 43 from the base 9 and the remaining interior of the patch pump 1 to protect particles or fluid contamination from entering the fluid path inside the filling member 43. This arrangement advantageously provides appropriate sealing for the filling member 43 while minimizing the number of internal components and simplifying the overall design of the patch pump 1. Additionally, if an adhesive is used to secure the filling member 43 to the base 9, the septum 18 prevents the adhesive at the interface of the filling member 43 and the base 9 from entering the filling member 43 and contaminating the medicament.

According to one embodiment, a user inserts a portion of a medicament container, such as a needle of a syringe, into the filling member 43 by piercing through the septum 18. As a result, the portion of the medicament container enters into an interior of the filling member 43 to fill the filling member 43 with the medicament. The septum 18 creates a seal around the inserted medicament container to maintain protection of the medicament from foreign liquids, adhesives, and particles. The septum 18 also advantageously prevents the medicament from leaking during and after the filling of medicament into the filling member 43, as well as during insertion and removal of the medicament container, and during operation of the patch pump 1.

FIG. 13 illustrates a central communication region 22 above and adjacent to the septum cavity 16 that houses the septum 18. According to one embodiment, the region 22 is in fluid communication with a first conduit 12 and a second conduit 14. The first conduit 12 is a reservoir conduit that is in fluid communication with the reservoir 4. Accordingly, during filling, the medicament enters the region 22, travels into the first conduit 12, and travels into the reservoir 4. In this manner, the reservoir 4 is filled with medicament.

The reservoir 4 can either be a flexible reservoir or a rigid reservoir. Typically, a device having a rigid reservoir does not use a pump. Rather, a piston operates inside the rigid reservoir to drive the medicament out of the reservoir, into the flow path and through the various components of the device, and administer the medicament to the patient. On the other hand, a device having a flexible reservoir typically uses a pump within the device. The medicament is pulled from the reservoir by the pump, pushed through the various components of the device, and administered to the patient. Preferably, the patch pump 1 incorporates a flexible reservoir design where the reservoir 4 does not include a piston. Instead, the medicament is pulled from the reservoir 4 by the pump 3, and the pump 3 is external to the reservoir 4.

As illustrated in FIG. 13 according to one embodiment, while the reservoir 4 is being filled with medicament via the first conduit 12, the medicament also fills the second conduit 14 and the fluid pathway to an inflow portion (entrance) of the pump 3. Path 50 represents the medicament flow path when the medicament container pierces the septum 18. Path 52 represents the medicament flow path as the medicament fills the reservoir 4, the filling member 43 and the fluid path leading to the entrance of the pump 3. The medicament in path 52 travels to the reservoir 4 and to the pump 3 substantially simultaneously. Path 54 represents the medicament flow path during operation of the patch pump 1. During operation, the medicament exits the reservoir 4, travels through the first conduit 12, the region 22 and the second conduit 14, and ultimately exits the filling member 43 to various components of the patch pump 1.

The second conduit 14 is a pump conduit that is in fluid communication with the pump 3. In the assembled state of one embodiment, the second conduit 14 is a narrow passageway that is located above the base 9. The first and second conduits 12, 14 intersect at the region 22, and are substantially perpendicular to each other. One skilled in the art would understand, however, that the first and second conduits 12, 14 can have other angular relationships, or other positions relative to each other, without departing from the scope of the present invention. Path 50 advantageously establishes fluid communication with the first and second conduits 12, 14 and the region 22 when the medicament container pierces the septum 18.

As previously noted, the first and second conduits 12, 14 are in fluid communication with each other via the region 22. In this manner, when the reservoir 4 is being filled with the medicament, the first and second conduits 12, 14, the region 22 and the flow path leading to the pump 3 are substantially simultaneously filled with medicament (see path 52). Accordingly, the filling member 43 advantageously allows the reservoir 4 and the pump 3 to be in fluid communication with each other.

The patch pump 1, according to one embodiment, advantageously provides two-way medicament flow via the first conduit 12. Specifically, as previously described and as illustrated in FIG. 13, the medicament enters the reservoir 4 via the first conduit 12 and path 52. During operation of the patch pump 1, the medicament exits the reservoir 4 into the first conduit 12, travels to the region 22 via path 54, and enters the second conduit 14 of the filling member 43. Thus, the medicament flows through the first conduit 12 in two separate directions, path 52 and path 54, providing two-way medicament flow. Such a configuration advantageously provides simplicity in design and a reduction in the number of components within the patch pump 1.

According to one embodiment, the user inserts the portion of the medicament container into the filling opening 20 and penetrates the septum 18 to advantageously establish fluidly communication between the first and second conduits 12, 14, the region 22 and the reservoir 4. During operation, however, the septum 18 seals and prevents fluid communication between the first and second conduits 12, 14 of the filling member 43 and the filling opening 20 in the base 9. Such a configuration advantageously provides selective fluid communication between the filling member 43 and the filling opening 20 to ensure liquid sealing and prevent adhesive or particles from mixing with the medicament.

When the medicament exits the second conduit 14, the medicament preferably enters into a passageway 27 in the base 9, as shown in FIG. 12. According to one embodiment, the passageway 27 is a through hole and is substantially parallel to the first conduit 12. During operation, the medicament in the passageway 27 is pulled by the pump 3 and subsequently travels into the first fluid channel 24 at the bottom surface 23 of the base 9. FIGS. 8, 9 and 12 illustrate an exemplary embodiment of the medicament flow path in the fluid channels 24, 26 that communicate with the pump 3 and ultimately travel to the cannula 47 via the insertion mechanism 7. Accordingly, during operation of the patch pump 1, the medicament flows from the reservoir 4 to the first conduit 12, the region 22, the second conduit 14, the passageway 27, the fluid channels 24, 26, and the pump 3, and then to the insertion mechanism 7 and the cannula 47.

The cannula 47 receives the medicament from the pump 3 via the fluid channels 24, 26 and delivers the medicament into the skin of a patient. A porous frit is commonly used in the industry to block the needle end of a cannula. The porous fit creates back pressure in a device that incorporates a rigid reservoir to allow the rigid reservoir to be filled with medicament. Upon operation of the device having the rigid reservoir, the porous frit is manually removed by a health care professional or a user. Subsequently, the piston in the rigid reservoir is driven to begin administering the medicament to the patient. The porous frit is applied for a single use.

Preferably, the patch pump 1 does not use a porous frit. Because the patch pump 1 uses a pump 3 that is separate from a flexible reservoir 4, and intervenes in the medicament flow path between the reservoir 3 and the cannula 47, a porous frit is not necessary to apply back pressure. Rather, the pump 3 blocks the fluid path to the cannula 47 during filling so that the reservoir 4 is filled with medicament. Additionally, during operation of the patch pump 1, the pump 3 pulls the medicament from the reservoir 4 and drives the medicament to the cannula 47 to be administered to the patient. Thus, the pump 3 controls the flow of the medicament in the patch pump 1 and advantageously provides fluid communication among the reservoir 4, the filling member 43 and the cannula 47.

Figure 14:
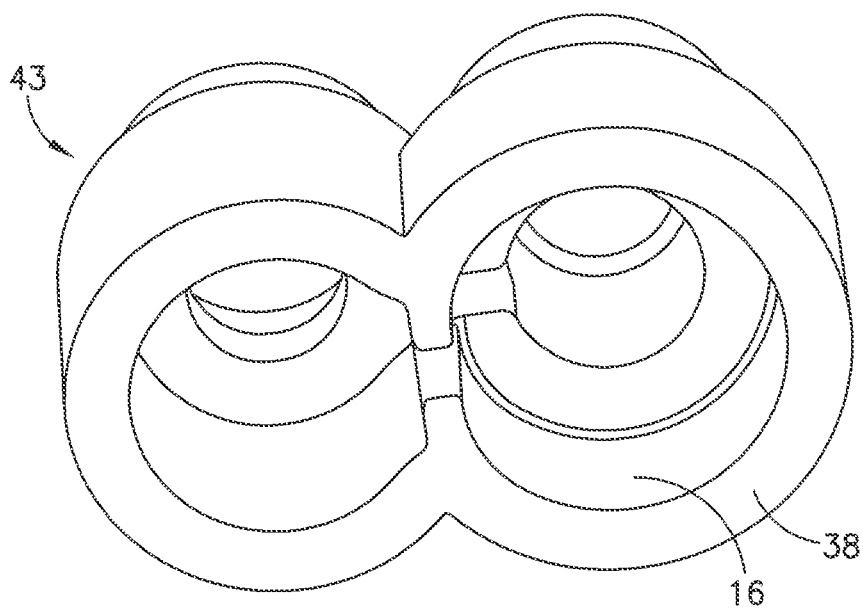
FIG. 14 is a bottom perspective view of melt collapse of the filling member.
Figure 15:
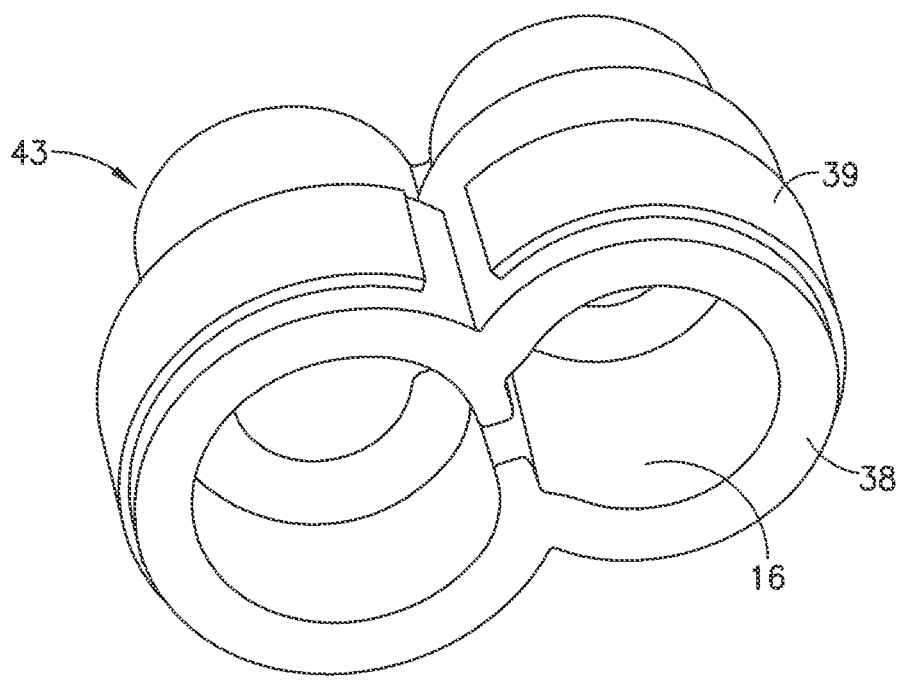
FIG. 15 is a bottom perspective view of a mechanical stop for melt collapse of the filling member.
Figure 16:
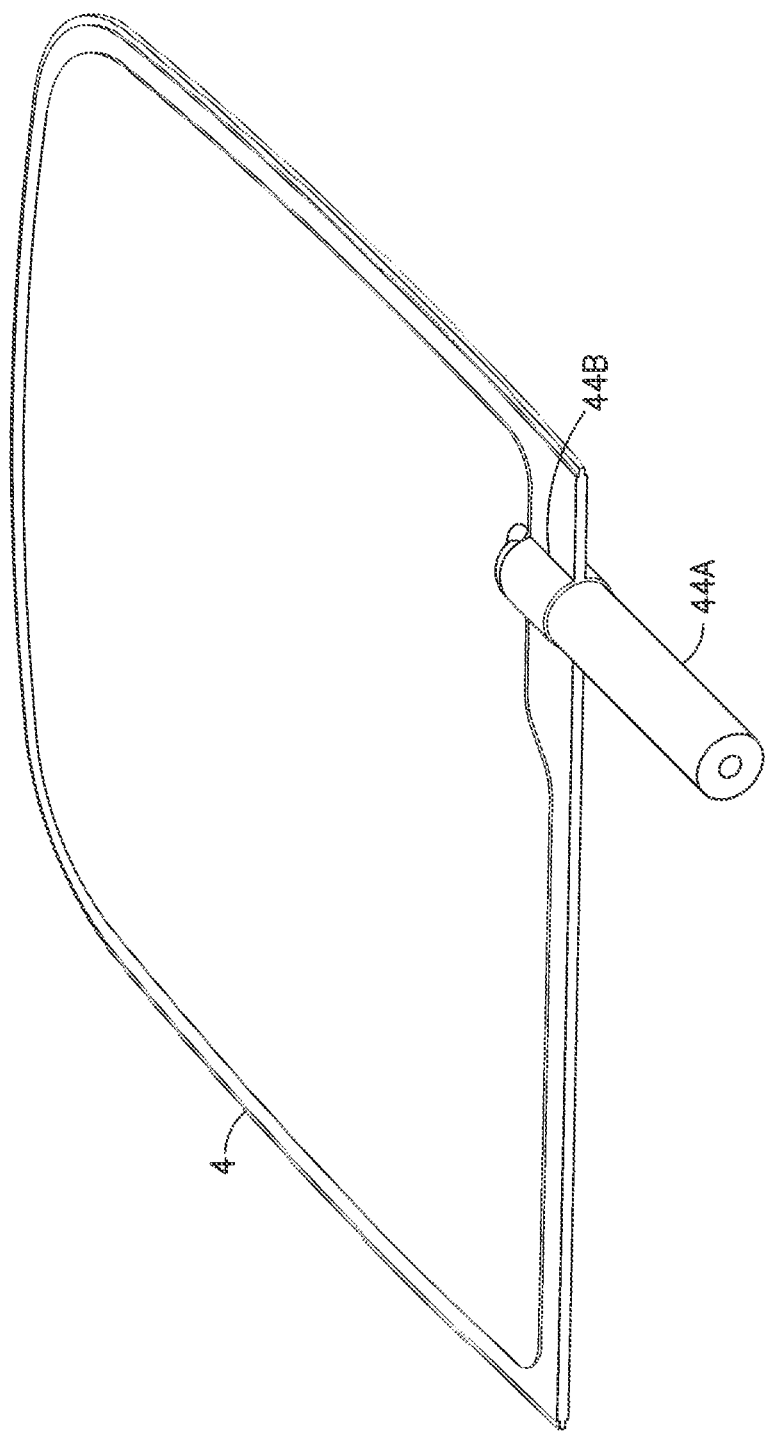
FIG. 16 is a perspective view of a reservoir tube connected to the reservoir.

FIGS. 14 and 15 illustrate melt collapse features of the filling member 43. Specifically, in FIG. 14, the filling member 43 includes a bottom surface 38 that is expected to collapse when the filling member 43 is laser welded to the base 9. In this manner, the melt collapse of the filling member 43 controls how much the septum 18 is compressed (see FIG. 12). Since the bottom surface 38 of the filling member 43 is subject to melt collapse, the septum 18 is only compressed axially and not radially.

FIG. 15 illustrates a skirt 39 that is placed around the septum cavity 16 at an outer surface of the filling member 47. The skirt 39 does not melt when the filling member 47 is laser welded to the base 9. Instead, the skirt 39 controls the melt collapse of the filling member 47 during laser welding to prevent the filling member 47 from radially contracting. As a result, the skirt 39 prevents the filling member 47 from radially collapsing at the septum cavity 16 and thus prevents any undesirable radial compression of the septum 18 (see FIG. 12).

FIGS. 16-19 depict alternative illustrative embodiments for a reservoir port connector or joint 44B that connects a reservoir tube 44A to the reservoir 4. The reservoir 4 is of a compact, smaller size compared to what is generally used in the industry. The reservoir 4 is a flexible, collapsible reservoir made from film materials ranging in thickness between 0.002-0.015 inches. The thickness can be varied depending on the need for structural integrity, flexibility, barrier properties, filling/emptying operational behavior and drug type. For example, material type and thickness can be selected to accommodate a selected pressure (e.g., which is affected by how much fluid is being delivered and by fluid properties), to preserve the integrity of reservoir 4 during shipping and handling, to achieve desired flexibility to conform to the reservoir port 44B or to a tube 44A and to prevent leakage of reservoir fluid, and/or to achieve a desired fill rate and/or volume.

Barrier properties include non-blocking characteristics that are considered in film material selection so that the film does not stick to itself as it collapses during emptying and blocks insulin flow. Barrier characteristic selection prevents contamination of the contents of the reservoir 4 (e.g., by external gases such as room air or fluids such as condensation). The material of the reservoir 4 can consist of one or more layers. For example, a three layer material can be used with an internal layer with properties conducive to heat sealing to a tube 44A and one or more outer layers having the afore-mentioned barrier properties or characteristics to prevent contamination of the contents of the reservoir 4 and protection of the integrity of the reservoir 4 during shipping, handling and use.

The film perimeter is sealed according to a variety of methods such as heat-sealing, radio frequency welding, laser welding, or other joining techniques that cause melting of the two film faces together. The preferred material of the reservoir 4 is sealed Air M312A film that is heat sealed. This material is advantageously compatible to insulin over an extended period of time up to at least three days. Additionally, the reservoir 4 is packaged with an oil film to protect the reservoir 4 during storage and prior to operation.

The reservoir 4 can be formed in a variety of ways. According to one embodiment, the reservoir 4 is formed by using two film sheets at each of the top and bottom surfaces that flexibly goes around the reservoir tube 44A. Such a configuration can provide optimal sealing between the reservoir 4 and the reservoir tube 44A. According to another embodiment, the reservoir 4 is formed by folding a single film on one edge and sealing the remaining edges. In another embodiment, the reservoir 4 may be formed by taking a tubular film and sealing at two opposite ends. The reservoir 4 is formed in another embodiment by using a rigid backing on the top surface and a flexible film on the bottom surface. During the perimeter sealing process, the reservoir 4 can be formed in any desired shape. The reservoir 4 can also be formed to include features to enable attachment to specific anchor points in the patch pump 1 for mounting purposes. The reservoir 4 satisfies industry sterilization and aging requirements and all operational loads/conditions.

A reservoir tube 44A is attached to the reservoir 4 on one end (e.g., forming a reservoir port connector or joint 44B), and to the filling member 43 at the other end. According to one embodiment, the reservoir tube 44A is a rigid port connection. Specifically, the reservoir tube 44A is laser welded to the reservoir 4 and the filling member 43 at each end. According to another embodiment, the reservoir tube 44A is a flexible port connection that is heat sealed to the reservoir 4. According to another embodiment, the reservoir tube 44A is molded or formed with the reservoir 4. For example, the processes of heat sealing, molding or forming the reservoir tube 44A and the reservoir 4 simultaneously advantageously improves manufacturability and sealing effectiveness. In another embodiment, the reservoir tube 44A is mechanically pressed to the reservoir 4. Finally, another embodiment adhesively bonds the reservoir tube 44A to the reservoir 4.

The reservoir tube 44A is preferably made of a tubular material commonly known in the industry as Teknor Apex MD-50273 or similar material. This material is compatible to the material of the reservoir 4 and the insulin. Similar to the reservoir 4, the reservoir tube 44A also satisfies industry sterilization and aging requirements and all operational loads/conditions. The reservoir tube 44A can be of a variety of cross-sectional shapes that facilitates sealing to the film material of the reservoir 4. Such shapes include round and oval shaped with varying degrees of tapered ends.

Figure 17:
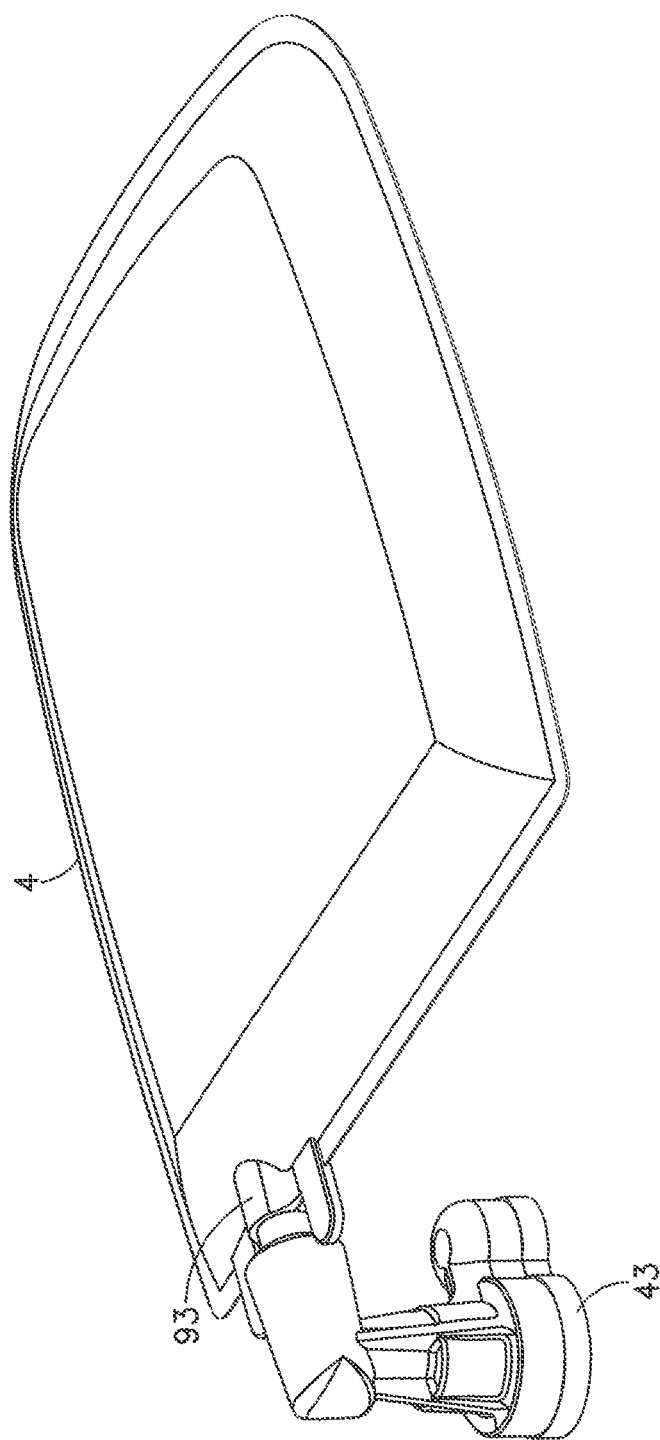
FIG. 17 is perspective view of the reservoir connected to the filling member.
Figure 18:
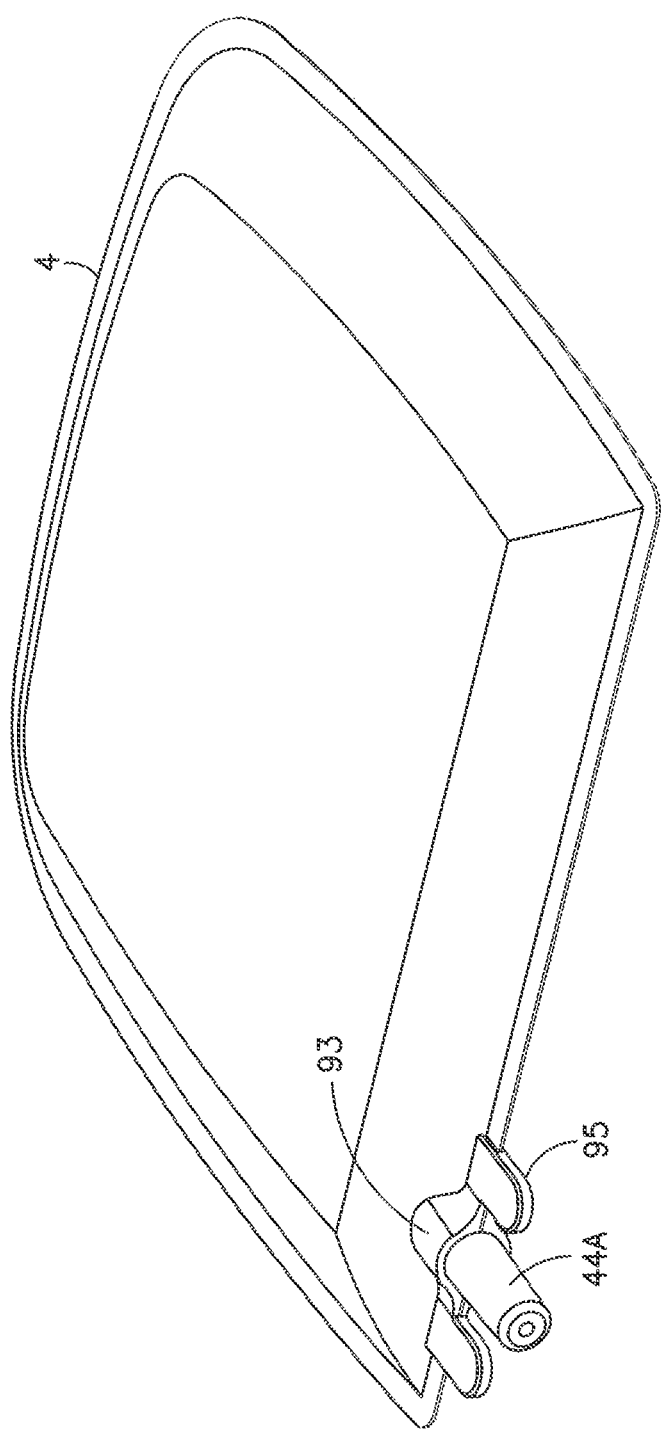
FIG. 18 is a perspective view of the reservoir and a receptacle used to connect to the filling member, in accordance with an illustrative embodiment of the present invention.
Figure 19:
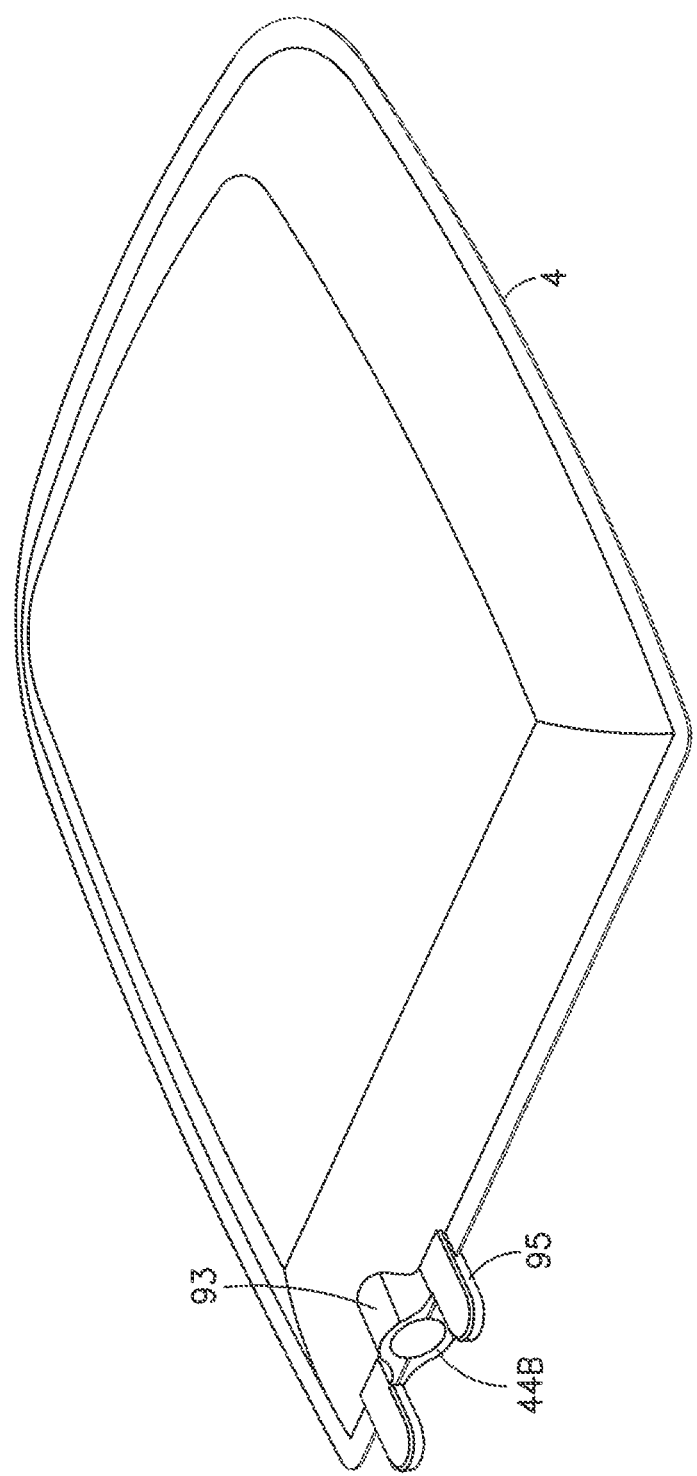
FIG. 19 is a perspective view of the reservoir without the receptacle.

A flexible port connector or joint 44B can be heat sealed by applying heat and pressure to join two parts at a joining surface (joint). Specifically, the joint 44B is where the reservoir tube 44A is sealed directly into the perimeter seal of the reservoir 4. In accordance with another embodiment of the present invention as shown in FIGS. 17-19, a receptacle 93 can be used that includes flanges 95 that join at the perimeter seal of the reservoir 4. Regardless of which embodiment is used, the joint 44B is advantageously leakproof and can withstand mechanical vibrations, loads and pressures such as when the patch pump 1 is in operation and worn by the user. Additionally, heat sealing advantageously provides greater flexibility in port configurations considered for connection. The other end of the reservoir tube 44A is press fitted to the filling member 43. This embodiment advantageously provides only mechanical assembly, which improves and simplifies the overall reservoir assembly. The mechanical connections also advantageously remove the use of adhesives and provide flexibility in positioning the reservoir port connector or joint 44B and the filling member 43.

Figure 20:
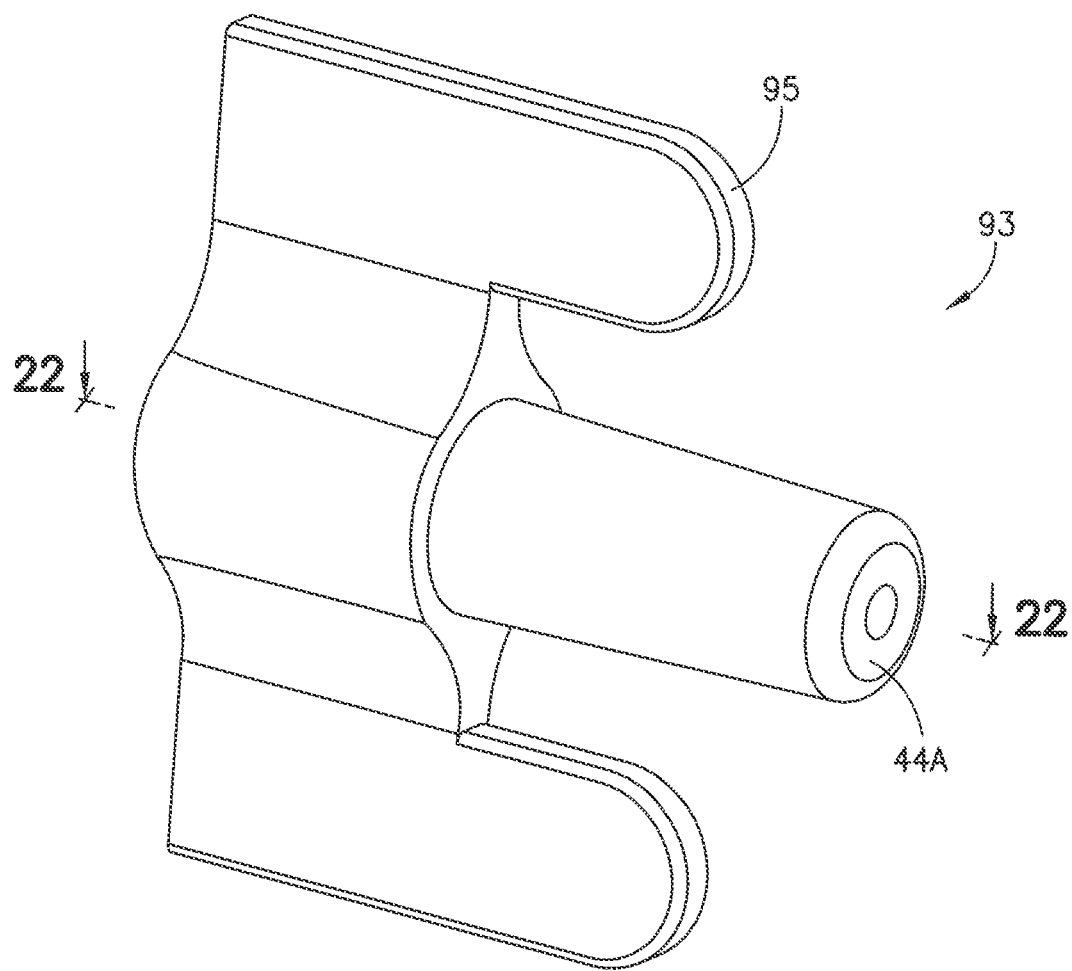
FIG. 20 is a perspective view of the receptacle.
Figure 21:
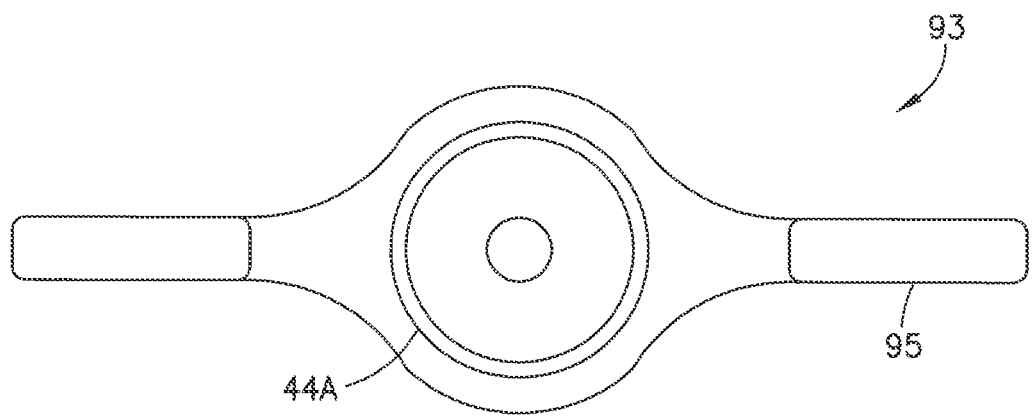
FIG. 21 is a front view of the receptacle.
Figure 22:
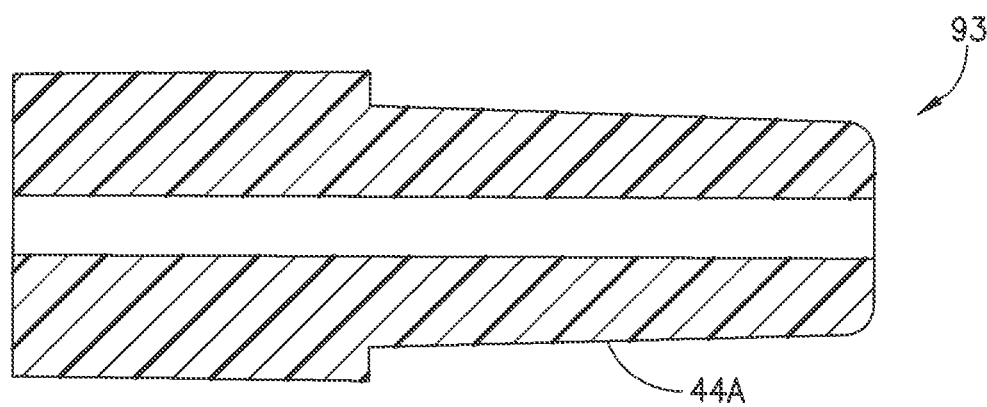
FIG. 22 is a cross-sectional view of the receptacle taken along line 22-22 of FIG. 20.

FIGS. 20-22 illustrate the receptacle 93 in more detail. In particular, the receptacle 93 can include the flexible reservoir tube 44A as a single unitary structure, or as a separate tube that is press fit or otherwise secured to a recess of the receptacle 93. Two flanges 95 are disposed on either side of the receptacle 93 to increase the surface area and thus strengthen the bond between the receptacle 93 and the reservoir 4 as described above. Additionally, the two flanges 95 improve assembly of the reservoir 4 because the flanges 95 provide a surface for a user to hold the receptacle 93.

FIG. 22 illustrates a cross sectional view of the receptacle 93. The flexible reservoir tube 44A of the receptacle 93 has a first diameter and the body of the receptacle 93 has a second diameter. The first diameter is preferably smaller than the second diameter.

According to one embodiment, the reservoir port connector or joint 44B of FIG. 19 can include filters to eliminate air in the flow path of the patch pump 1 and to improve sterilization. The reservoir film may further include an integral filter or vent film attached by heat sealing, mechanical or chemical joining to also aid to eliminate air in the patch pump 1 and to provide a more sterile environment.

In operation, the reservoir 4 is prefilled in a device or filled in the patch pump 1 prior to use by providing an appropriate filling port. When the flexible reservoir 4 is filled, it will expand to a final, filled shaped that is dependent on material properties, size and shape. When the reservoir 4 is connected to the pump 3 during operation, the fluid is driven and withdrawn from the reservoir 4. The reservoir 4 generally immediately collapses (self-collapsing) by an amount equal to the volume of fluid removed. The flexibility of the film of the reservoir 4 allows for the emptying (reservoir collapsing) behavior. The flexibility of the reservoir 4 advantageously provides optimal use of the internal volume of the patch pump 1. The fluid subsequently travels to the filling member 43 upon exiting the reservoir 4 and the receptacle 93.

Figure 23:
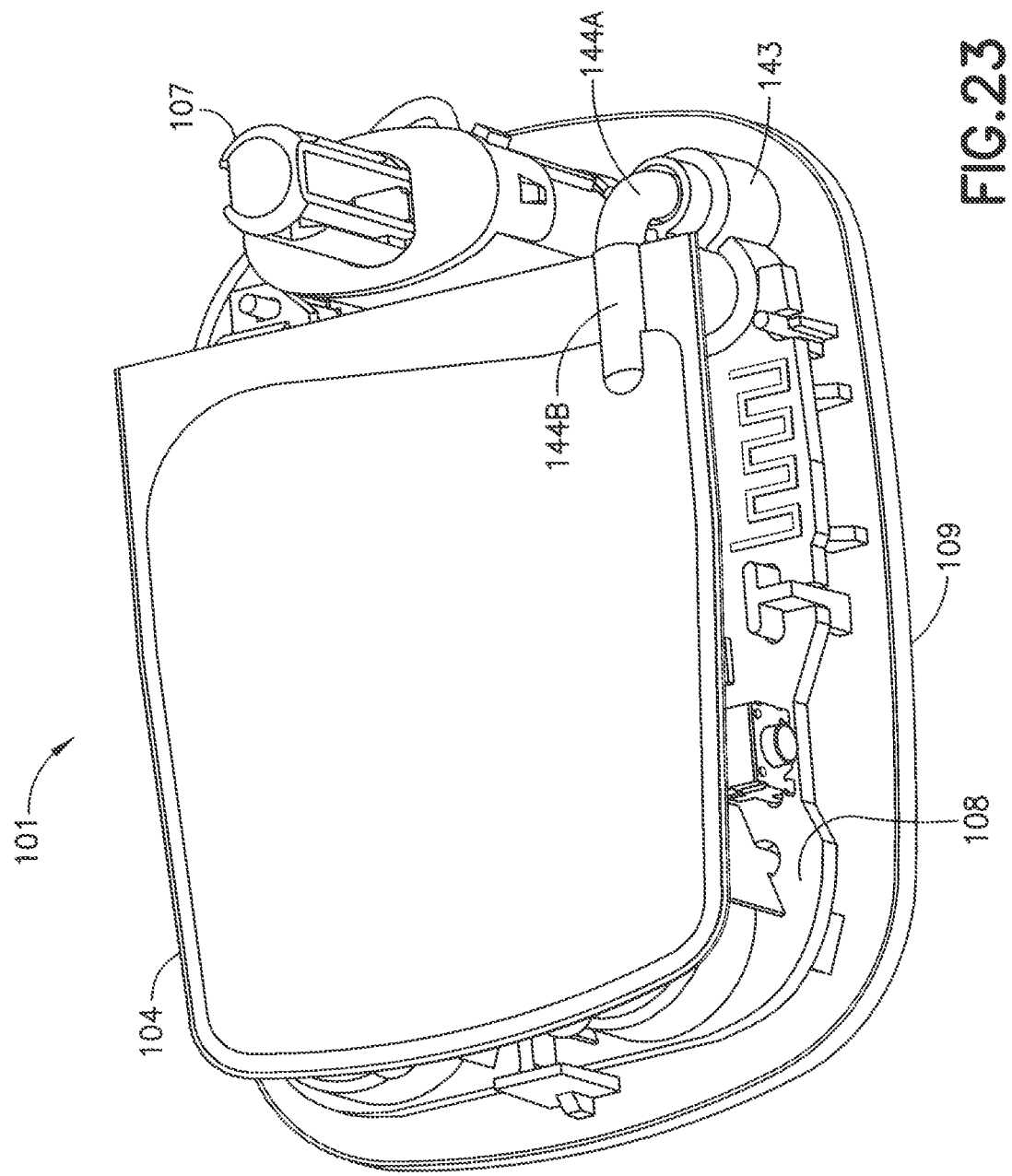
FIG. 23 is a perspective view of another embodiment of a patch pump, omitting a cover.

FIGS. 23-29 illustrate an alternate embodiment of the patch pump 101 that is similar to the patch pump 1 illustrated in the embodiments of FIGS. 8-13 and FIG. 16 with the following distinctions. FIG. 23 is a perspective view of another embodiment of a patch pump 101, omitting a cover. The patch pump 101 includes a filling member 143 directly connected to a reservoir 104 via a flexible reservoir tube 144A engaging a reservoir port connector 144B in the reservoir 104. The filling member 143 is also in fluid communication with the base 109.

Figure 24:
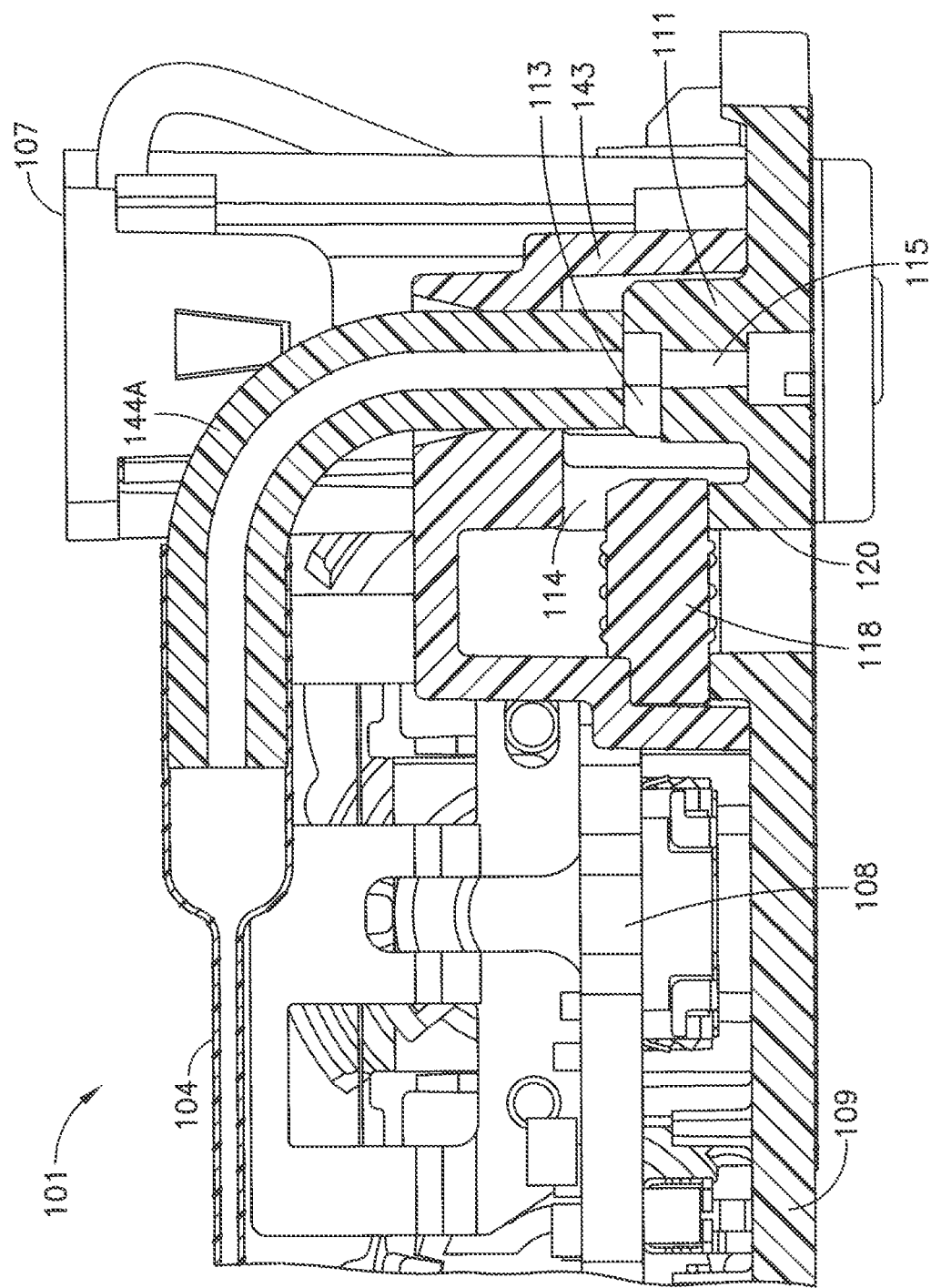
FIG. 24 is a partial cross-sectional view of the filling member in the patch pump of FIG. 23.
Figure 25:
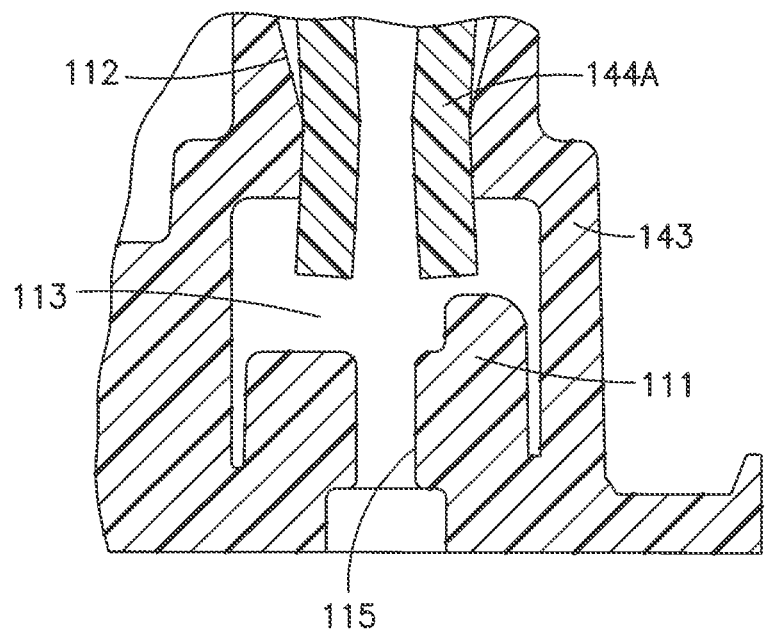
FIG. 25 is a cross-sectional view of the filling member attached to the reservoir tube.
Figure 26:
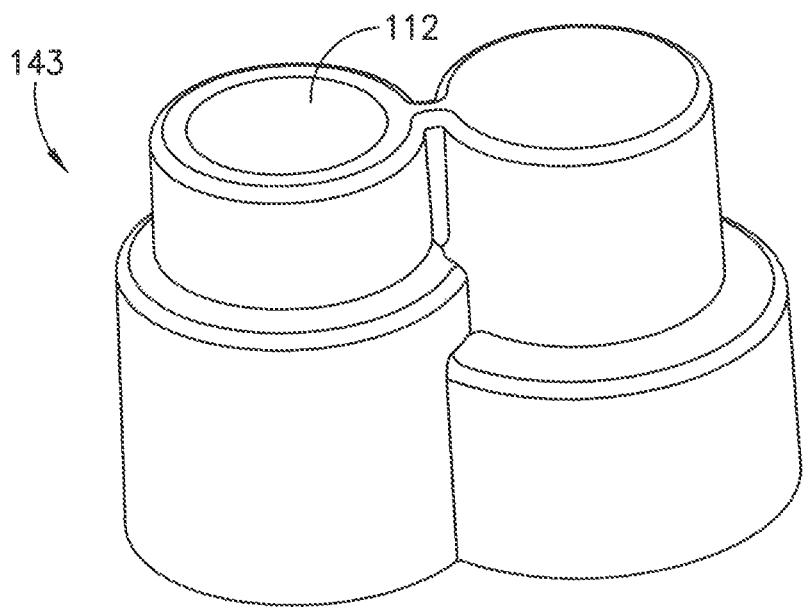
FIG. 26 is a top perspective view of a filling member in the patch pump of FIG. 23, in accordance with an illustrative embodiment of the present invention.
Figure 27:
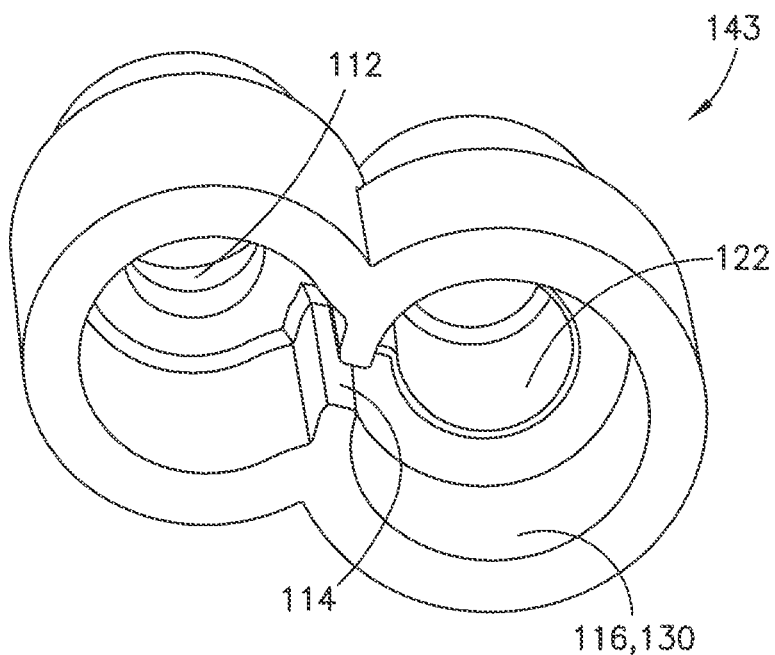
FIG. 27 is a bottom perspective view of the filling member of FIG. 26.
Figure 28:
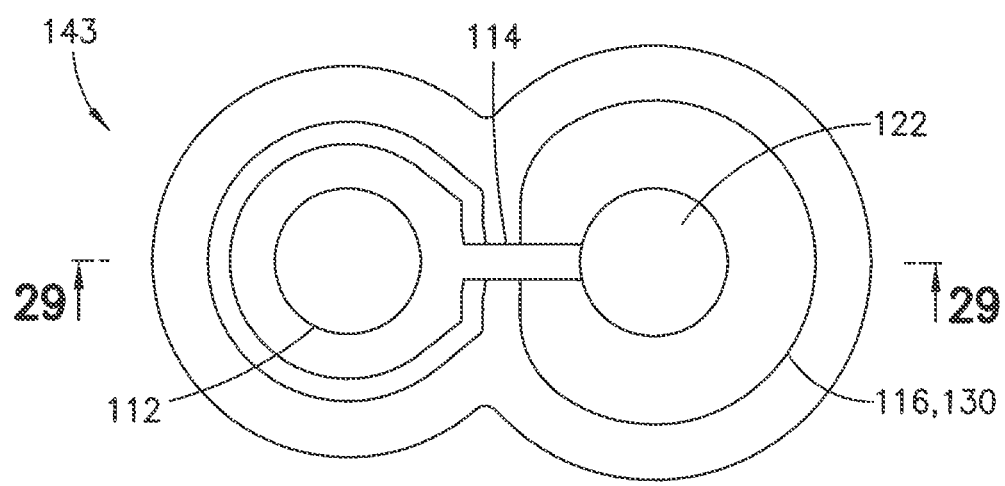
FIG. 28 is a bottom view of the filling member of FIG. 26.

FIG. 24 is a partial cross-sectional view of the filling member 143 in the patch pump 101 of FIG. 23. The base 109 is preferably clear and laser transmissive. The base 109 includes a protruding portion 111 that extends from a bottom portion of the base 109 and is disposed in the filling member 143. As illustrated in FIGS. 24 and 25, the protruding portion 111 in the base 109 includes a through hole 115 that provides fluid communication between a pump and the reservoir 104. The distal end of the protruding portion 111 includes a slot 113. When the filling member 143 is being filled with medicament, the slot 113 receives the medicament and directs the medicament to the pump and the reservoir 104. The operation of the filling member 143 is described in further detail below.

The reservoir 104 is preferably flexible, as described above, and is connected to the filling member 143 via the flexible tubing 144A. As illustrated in FIGS. 24 and 25, the flexible tubing 144A is mechanically pressed to the filling member 143 by an interference fit. As a result, no adhesives are used to secure the flexible tubing 144A to the filling member 143. This advantageously improves assembly and prevents adhesive from mixing with the medicament. The interference fit also meets sterilization requirements, aging requirements and all operation loads and conditions of the patch pump 101.

The protruding portion 111 in the base 109 is advantageously positioned in the filling member 143 to control the end position of the flexible tubing 144A while establishing fluid communication. Specifically, the flexible tubing 144A contacts or bottoms out on a top surface of the protruding portion 111. This contact advantageously ensures proper mechanical capture of the flexible tubing 144A in the filling member 143. Accordingly, fluid from the reservoir 104 travels through the flexible tubing 144A, into the protruding portion 111 and into the flow channels.

A septum 118 is disposed in the filling member 143. The filling member 143, as illustrated in FIGS. 26-29, includes a septum cavity 116 having an inner diameter septum cavity wall 130 that secures the septum 118. The inner diameter septum cavity wall 130 is specifically sized to axially trap the septum 118 in the filling member 143. The septum 118 is then secured between the filling member 143 and the base 109 to create a full seal. The septum 118 is compressed and sealed in the axial direction only and not radially. Specifically, the filling member 143 collapses a controlled amount during laser welding to set the proper compression for the septum 118 while considering all part and process tolerances. Such a configuration improves assembly and reduces the manufacture of critical features while providing optimal sealing.

Additionally, a centerline of the septum 118 is disposed substantially parallel to and offset from a centerline of the flexible tubing 144A and a centerline of a protruding portion 111 of the base 109. This configuration advantageously prevents the flexible tubing 144 from contacting the medicament container when filling the filling member 143. Specifically, if the flexible tubing 144A and the septum 118 are in-line, the user may possibly inadvertently push the flexible tubing 144A out of the filling member 143 when the septum 118 is pierced with a portion of a medicament container to fill the filling member 143 with medicament as described above. Accordingly, this configuration avoids the inadvertent movement of the flexible tubing 144A after securement to the filling member 143.

After the septum 118 is installed into the filling member 143 and the base 109, the filling member 143 is secured to the base 109 preferably via laser welding. The filling member 143 includes laser absorbent additives to facilitate laser welding.

Figure 29:
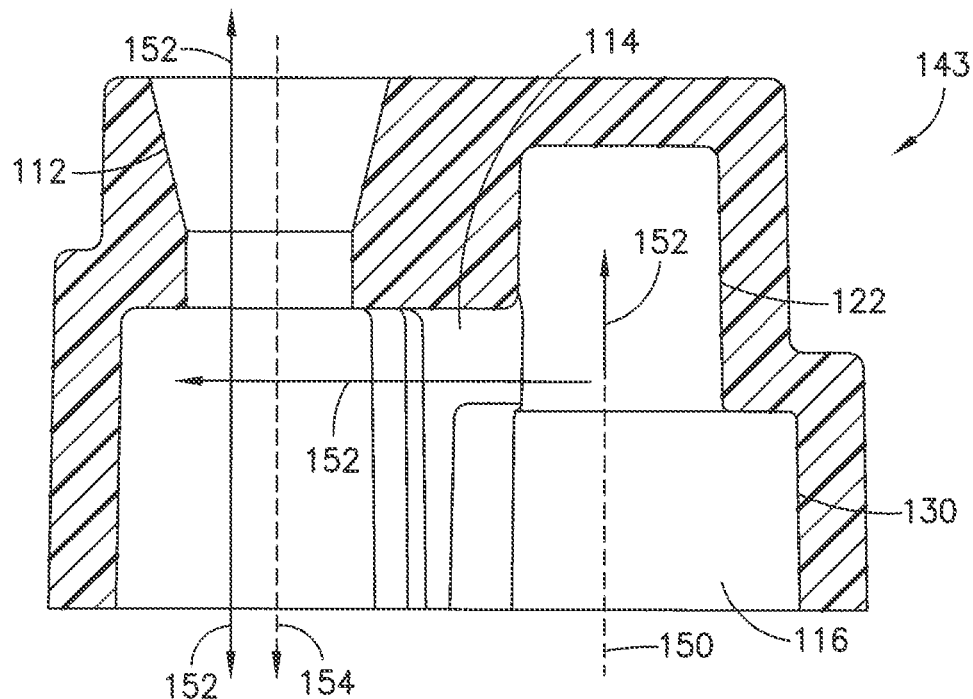
FIG. 29 is a cross-sectional view of the filling member taken along line 29-29 of FIG. 28.

As illustrated in FIGS. 26-29, and similar to the embodiment disclosed above, the filling member 143 includes a first conduit 112, a second conduit 114, as well as a region 122 adjacent to the septum 118. The medicament fills the first and second conduits 112, 114 in order to fill the reservoir 104 and the fluid pathway to an inflow portion (entrance) of the pump with medicament. As illustrated in FIG. 29, path 150 represents the medicament flow path when the medicament container pierces the septum 118. Path 152 represents the medicament flow path as the medicament fills the reservoir 104, the filling member 143 and the fluid path leading to the entrance of the pump. The medicament in path 152 travels to the reservoir 104 and to the pump substantially simultaneously. Path 154 represents the medicament flow path during operation of the patch pump 101.

During operation, the medicament exits the reservoir 104, travels through the reservoir tube 144A and the protruding portion 111 of the base 109 disposed in the first conduit 112 and ultimately exits the filling member 143 to various components of the patch pump 101. A centerline of the reservoir tube 144A and a centerline of the protruding portion 111 of the base 109 are substantially parallel to and in-line with a centerline of the first conduit 112.

The second conduit 114 is a filling conduit that provides one way fluid communication with the first conduit 112 during filling. In the assembled state of one embodiment, the second conduit 114 is a narrow passageway that is located above the protruding portion 111 of the base 109. The first and second conduits 112, 114 are substantially perpendicular to each other. One skilled in the art would understand, however, that the first and second conduits 112, 114 can have other angular relationships, or other positions relative to each other, without departing from the scope of the present invention. Path 150 advantageously establishes fluid communication with the first and second conduits 112, 114 and the region 122 when the medicament container pierces the septum 118.

As previously noted, the first and second conduits 112, 114 are in fluid communication with each other during filling. When the reservoir 104 is being filled with the medicament, the first and second conduits 112, 114, the region 122 and the flow path leading to the pump are substantially simultaneously filled with medicament (see path 152). Accordingly, the filling member 143 advantageously allows the reservoir 104 and the pump to be in fluid communication with each other.

The patch pump 101, according to one embodiment, advantageously provides two-way medicament flow via the first conduit 112. Specifically, the medicament enters the reservoir 104 via the first conduit 112 and path 152. During operation of the patch pump 101, the medicament exits the reservoir 104 into the first conduit 112 via the reservoir tube 144A and the protruding portion 111 of the base 109. Thus, the medicament flows through the first conduit 112 in two separate directions, path 152 and path 154, providing two-way medicament flow. Such a configuration advantageously provides simplicity in design and a reduction in the number of components within the patch pump 101.

According to one embodiment, the user inserts the portion of the medicament container into the filling opening 120 and penetrates the septum 118 to advantageously establish fluidly communication between the first and second conduits 112, 114, the region 122 and the reservoir 104. During operation, however, the septum 118 is closed and prevents fluid communication between the first conduit 112 and the filling opening 220 in the base 109. That is, the second conduit 114, the region 122 and the slot 113 in the protruding portion 111 of the base 109 are not used during medication delivery. The region 122 acts as a dead volume where a substantial amount of fluid is never removed because the filling member 143 cannot decapitate. In order to maintain pressure equilibrium of the filling member 143, a substantial amount of fluid does not exit the region 122, the second conduit 114 and the slot 113 during medication delivery. Such a configuration advantageously provides selective fluid communication between the filling member 143 and the filling opening 120, and streamlines medicament flow through the protruding portion 111, into various other components of the patch pump 101 and ultimately delivers the medicament as described above.

Figure 30:
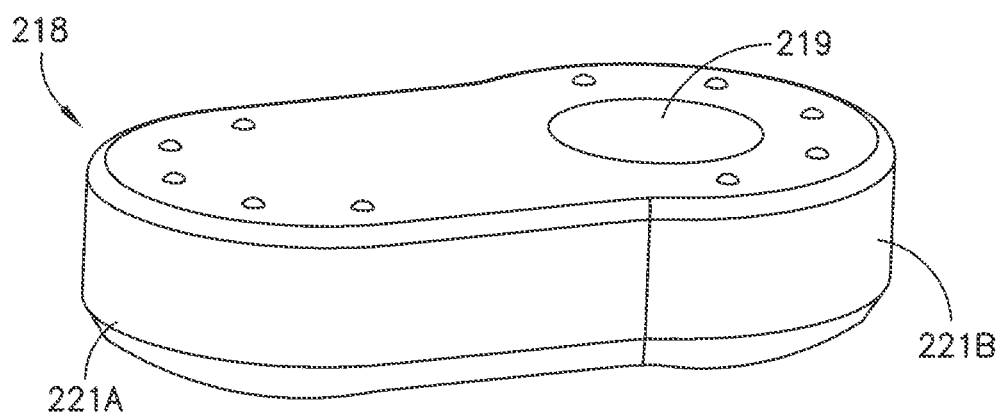
FIG. 30 is a perspective view of a septum in accordance with another illustrative embodiment of the present invention.
Figure 31:
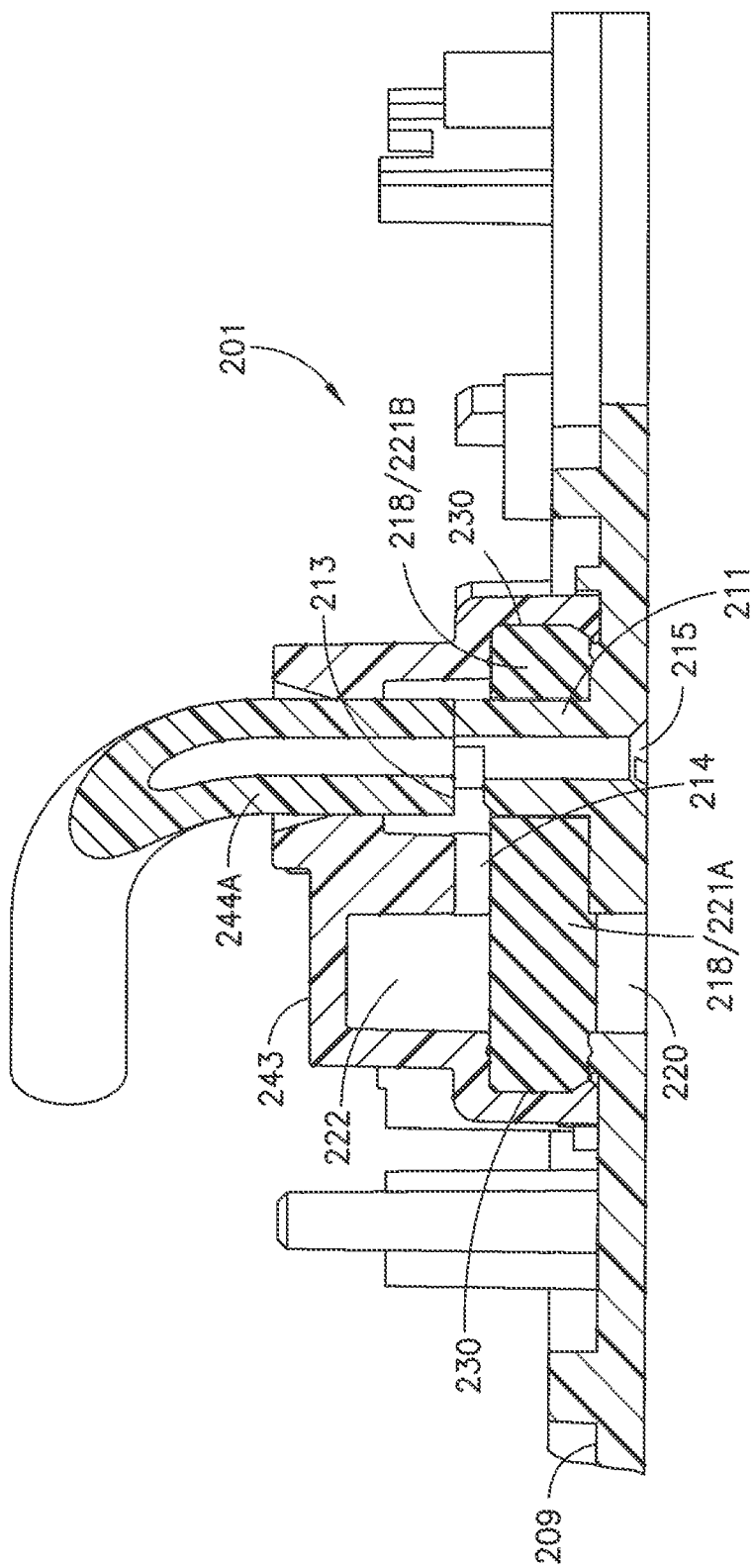
FIG. 31 is a partial cross-sectional view of the septum of FIG. 30 and the filling member in another embodiment of the patch pump of FIG. 23.

FIGS. 30 and 31 illustrate another embodiment of a keyhole septum 218 in a similar manner as described above. The keyhole septum 218 includes a first circular portion 221A and a second circular portion 221B. The second circular portion 221B of the keyhole septum 218 includes a through hole 219 that provides an additional sealing surface.

As illustrated in FIG. 31, the keyhole septum 218 is disposed in a filling member 243 and seals the filling member 243 at both a centerline axis of the reservoir tubing 244A and a centerline axis of region 222. Specifically, the through hole 219 in the first circular portion 221A of the keyhole septum 218 seals an outer diameter of a protruding portion 211 of a base 209. Also, the second circular portion 221B of the keyhole septum 218 seals at a septum cavity wall 230 of the filling member 243.

This arrangement advantageously allows for the preferable use of adhesive bonding between the base 209 and the filling member 243. Since the keyhole septum 218 seals at both of the interfaces described above, the risk of mixing adhesive with medicament is significantly reduced. Accordingly, the medicament does not contact and mix with the adhesive during operation. Specifically, the adhesive is not able to enter a filling opening 220 or travel past the septum 218 to mix with the adhesive. In this embodiment, the filling member 243 can also be laser welded to the base 209, although adhesive is preferred for processing advantages.

Although only a few embodiments of the present invention have been shown and described, the present invention is not limited to the described embodiments. Instead, it will be appreciated by those skilled in the art that changes may be made to these embodiments without departing from the principles and spirit of the invention. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

What is claimed is:

1. A filling member in a medicament delivery device, the filling member comprising:
   a first conduit that fluidly communicates with a reservoir and a pump, the first conduit configured to press fit to a reservoir tube;
   a second conduit that fluidly communicates with the first conduit to fill the filling member with medicament; and
   a septum cavity for housing a septum;
   wherein the filling member provides two-way medicament flow that:
      enters the reservoir via the first conduit and the second conduit;
      exits the reservoir into the first conduit;
      exits the first conduit to the pump; and
   the septum cavity does not compress the septum radially.

2. The filling member according to claim 1, wherein the second conduit is not used for medication delivery as the medicament exits the filling member to the pump.

3. The filling member according to claim 1,
   a centerline of the septum cavity is offset from and substantially parallel to a centerline of the first conduit.

4. The filling member according to claim 3, wherein the septum cavity compresses the septum a predetermined amount axially.

5. A device for delivering medicament into skin of a patient, the device comprising:
   a filling member including:
      a septum cavity for housing a septum;
      a first conduit that fluidly communicates with a reservoir and a pump, the first conduit configured to press fit to a reservoir tube;
      a second conduit that fluidly communicates with the first conduit to fill the filling member with medicament;
   wherein the filling member provides two-way medicament flow that:
      enters the reservoir via the first conduit and the second conduit;
      exits the reservoir into the first conduit;
      exits the first conduit to the pump; and
   the septum cavity does not compress the septum radially.

6. The device according to claim 5, wherein the medicament flow does not exit into the second conduit from the first conduit.

7. A device for delivering medicament into skin of a patient, the device comprising:
   a filling member including:
      a septum cavity for housing a septum;
      a first conduit that fluidly communicates with a reservoir and a pump;
      a second conduit that fluidly communicates with the first conduit to fill the filling member with medicament;
   a reservoir tube having one end that is formed with the reservoir; and the reservoir tube having another end that is press fit to the filling member to establish fluid communication with the reservoir;
   wherein
      the other end of the reservoir tube contacts a protruding portion of a base; and
      the filling member provides two-way medicament flow that:
         enters the reservoir via the first conduit and the second conduit;
         exits the reservoir into the first conduit; and
         exits the first conduit to the pump.

8. The device according to claim 7, wherein the protruding portion of the base is disposed in the filling member.

9. The device according to claim 7, wherein
   the protruding portion includes a slot; and
   the slot is in fluid communication with the second conduit of the filling member during filling.

10. The filling member according to claim 9, wherein the slot is not in fluid communication with the first conduit during medication delivery.

11. The device according to claim 7, wherein a centerline of the protruding portion of the base is substantially parallel to and offset from a centerline of the septum.

12. The device according to claim 7, wherein
   the protruding portion of the base includes a through hole; and
   the through hole of the protruding portion is substantially inline and in fluid communication with the first conduit.

13. The device according to claim 7, wherein the septum includes a hole that surrounds the protruding portion of the base to seal the filling member.

14. A medicament delivery device comprising:
   a cover and a base, the base including a protruding portion, the cover and the base enclosing:
      a pump that controls flow of medicament to a patient;
      a filling member including:
         a septum adapted to provide access to an interior of the filling member via penetration therethrough;
         a septum cavity for housing the septum;
         a first conduit that receives the protruding portion and fluidly communicates with a reservoir and the pump; and
         a second conduit that fluidly communicates with the first conduit to fill the filling member with medicament;
   wherein the filling member provides two-way medicament flow that:
      enters the reservoir via the first conduit and the second conduit;
      exits the reservoir into the first conduit; and
      exits the first conduit to the pump.

* * * * *